United States Patent [19]
Chu et al.

[11] Patent Number: 5,967,984
[45] Date of Patent: Oct. 19, 1999

[54] ULTRASOUND IMAGING CATHETER WITH A CUTTING ELEMENT

[75] Inventors: Michael S. H. Chu, Brookline; Yem Chin, Burlington, both of Mass.; Demetrius H. Bagley, Philadelphia, Pa.; William H. Stahley, Andover, Mass.; David K. Young, Boston, Mass.; Christopher G. Fishbein, Norfolk, Mass.; George G. Brusard, Cambridge, Mass.

[73] Assignee: Boston Scientific Corporation, Natick, Mass.

[21] Appl. No.: 08/757,848

[22] Filed: Nov. 27, 1996

Related U.S. Application Data

[63] Continuation of application No. PCT/US96/11139, Jul. 1, 1995, which is a continuation-in-part of application No. 08/497,465, Jun. 30, 1995, abandoned.

[51] Int. Cl.[6] .................................................. A61B 8/12
[52] U.S. Cl. ..................................... 600/439; 607/122
[58] Field of Search .................................. 600/437, 439, 600/463–464, 470–471; 606/41–45; 607/101, 122

[56] References Cited

U.S. PATENT DOCUMENTS

| | | | |
|---|---|---|---|
| 4,763,662 | 8/1988 | Yokoi ..................................... | 600/464 |
| 4,841,977 | 6/1989 | Griffith et al. .......................... | 600/470 |
| 4,951,677 | 8/1990 | Crowley et al. ........................ | 600/463 |
| 5,029,588 | 7/1991 | Yock et al. ............................. | 600/471 |
| 5,100,424 | 3/1992 | Jang et al. ............................. | 600/471 |
| 5,109,859 | 5/1992 | Jenkins ................................... | 600/470 |
| 5,167,233 | 12/1992 | Eberle et al. ........................... | 600/470 |
| 5,254,112 | 10/1993 | Sinofsky et al. ........................ | 600/471 |
| 5,255,679 | 10/1993 | Imran ..................................... | 607/122 |
| 5,345,940 | 9/1994 | Seward et al. ...................... | 600/471 X |
| 5,383,460 | 1/1995 | Jang et al. ......................... | 600/471 X |
| 5,485,846 | 1/1996 | Webler et al. .......................... | 600/463 |
| 5,588,432 | 12/1996 | Crowley et al. ........................ | 600/471 |
| 5,601,539 | 2/1997 | Corso, Jr. ............................... | 604/282 |
| 5,603,731 | 2/1997 | Whitney ................................. | 607/122 |
| 5,609,151 | 3/1997 | Mulier et al. ............................ | 606/27 |
| 5,628,746 | 5/1997 | Claymon ................................. | 606/45 |
| 5,687,723 | 11/1997 | Avitall ................................ | 607/122 X |

*Primary Examiner*—Francis J. Jaworski
*Attorney, Agent, or Firm*—Lyon & Lyon LLP

[57] ABSTRACT

The invention features a catheter having a catheter body of extended length for insertion within a body of a living being. The catheter also includes an ultrasound imaging device disposed within a distal portion of the catheter body. The ultrasound imaging device generates electrical signals used by an ultrasound imaging system to display a real-time image of tissue surrounding the distal portion of the catheter. The catheter further includes a cutting element, e.g., an electrode wire or a laser fiber, having a proximal portion disposed within the catheter body. The catheter also includes a mechanism connected to the catheter body that causes the distal portion of the cutting element to extend from the catheter body. The distal portion of the cutting element generates energy in tissue with which it is brought in proximity to form a cut in the tissue. The ultrasound imaging device is positioned relative to the cutting element such that the real-time image produced by the ultrasound imaging system can include the cutting element in relation to the tissue.

64 Claims, 18 Drawing Sheets

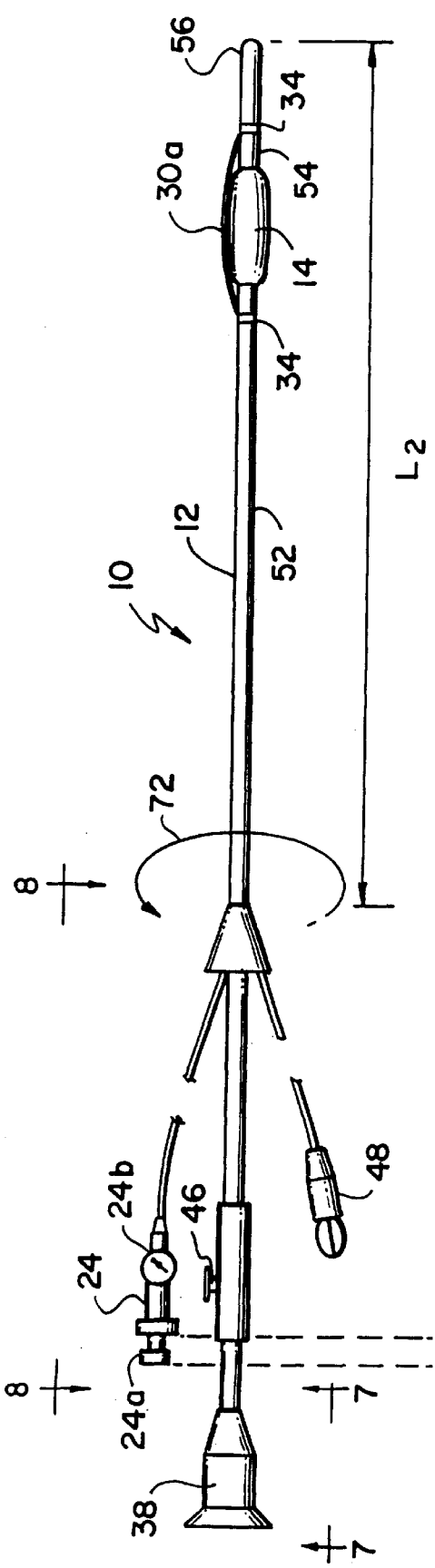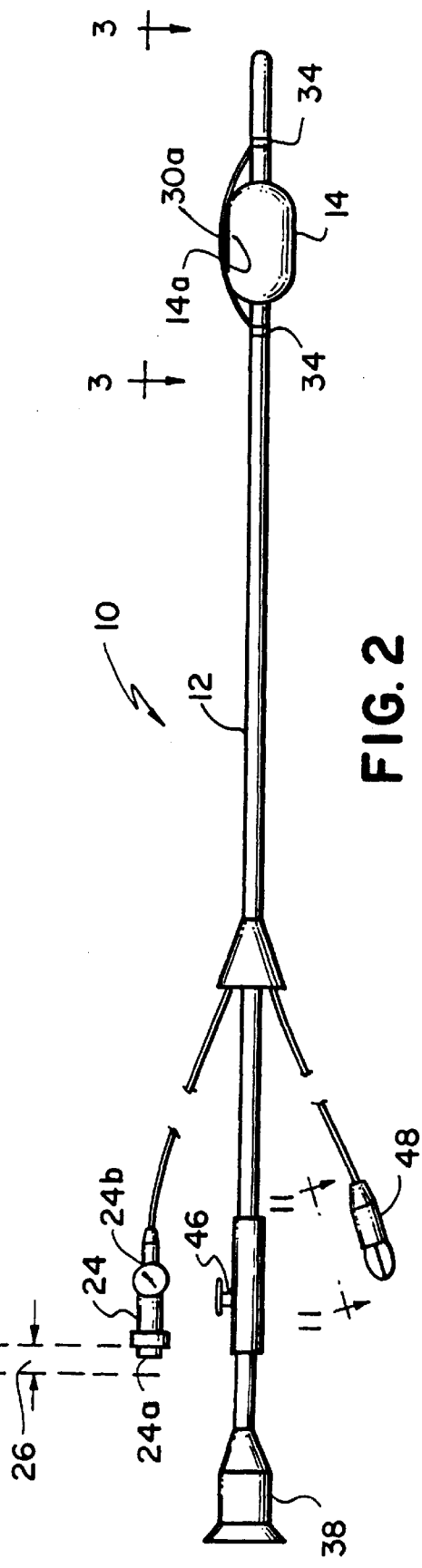

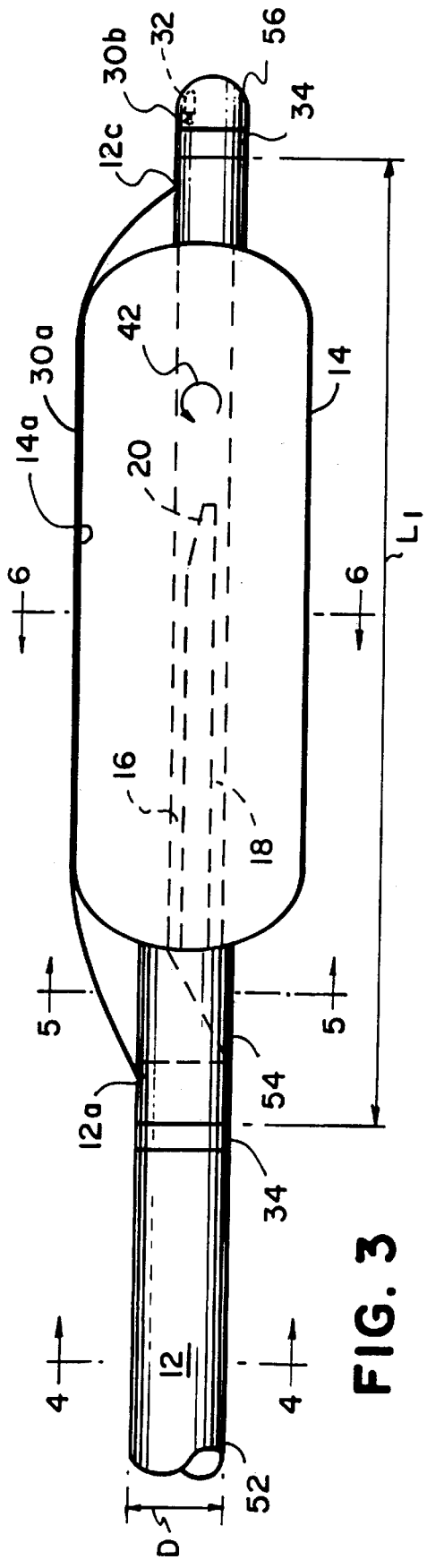
FIG. 3
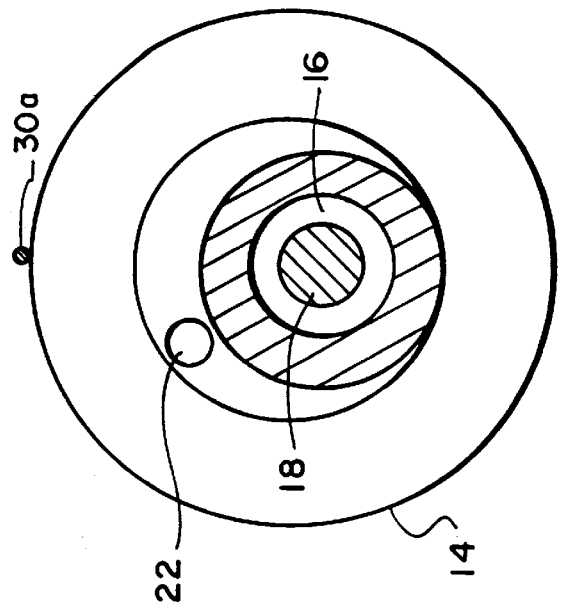
FIG. 6
FIG. 5
FIG. 4

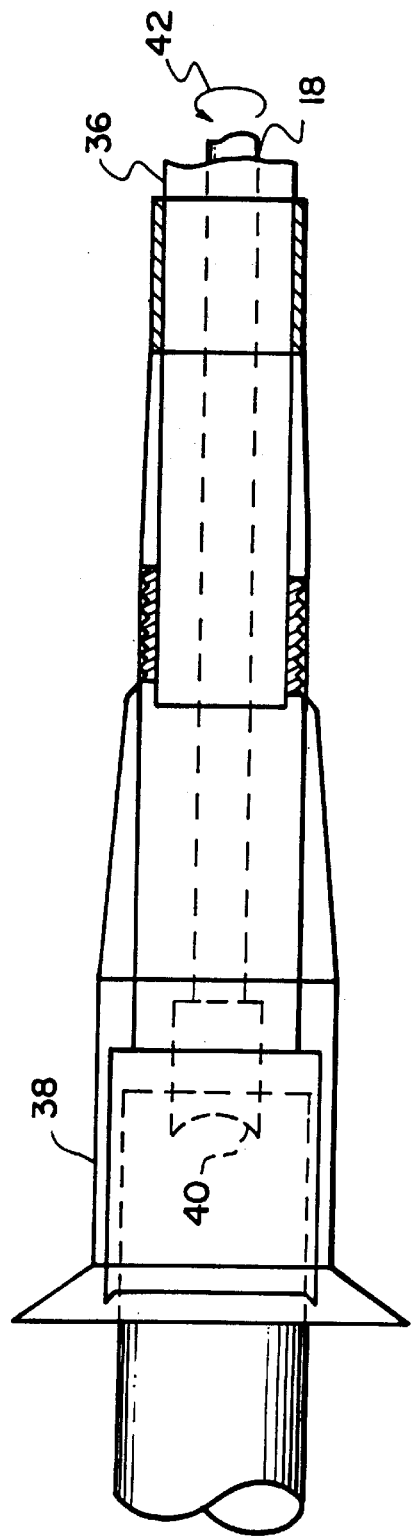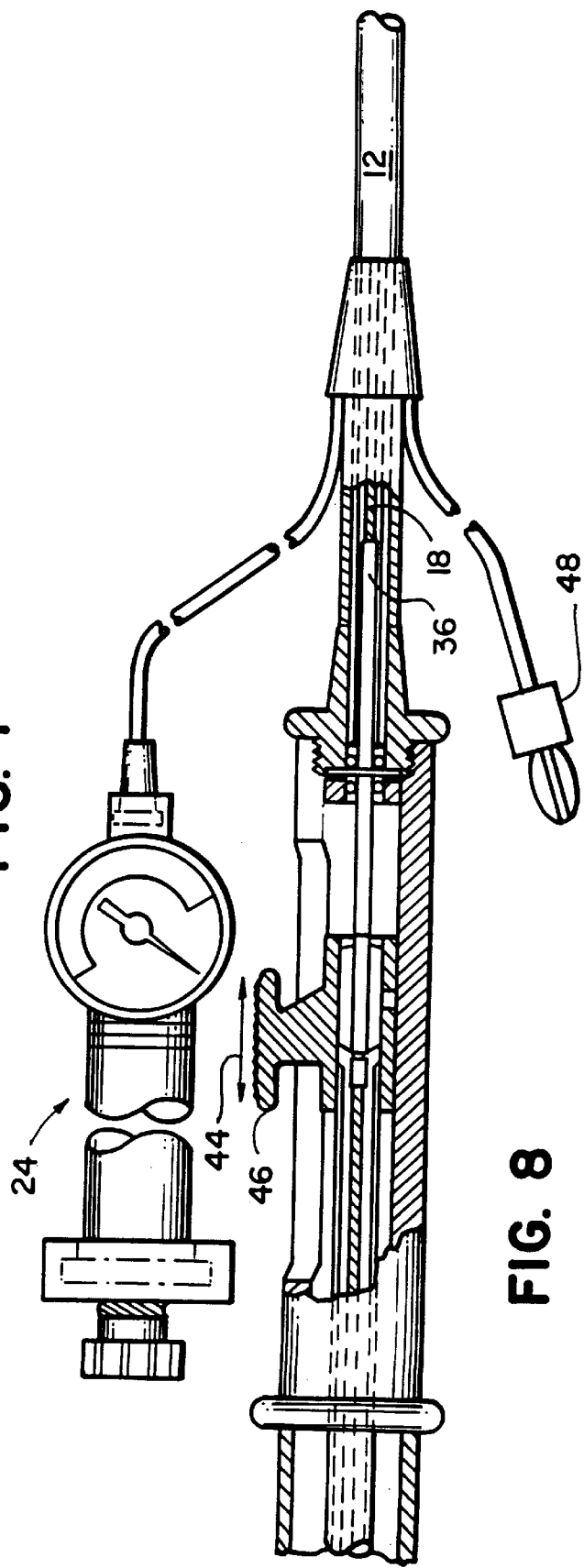

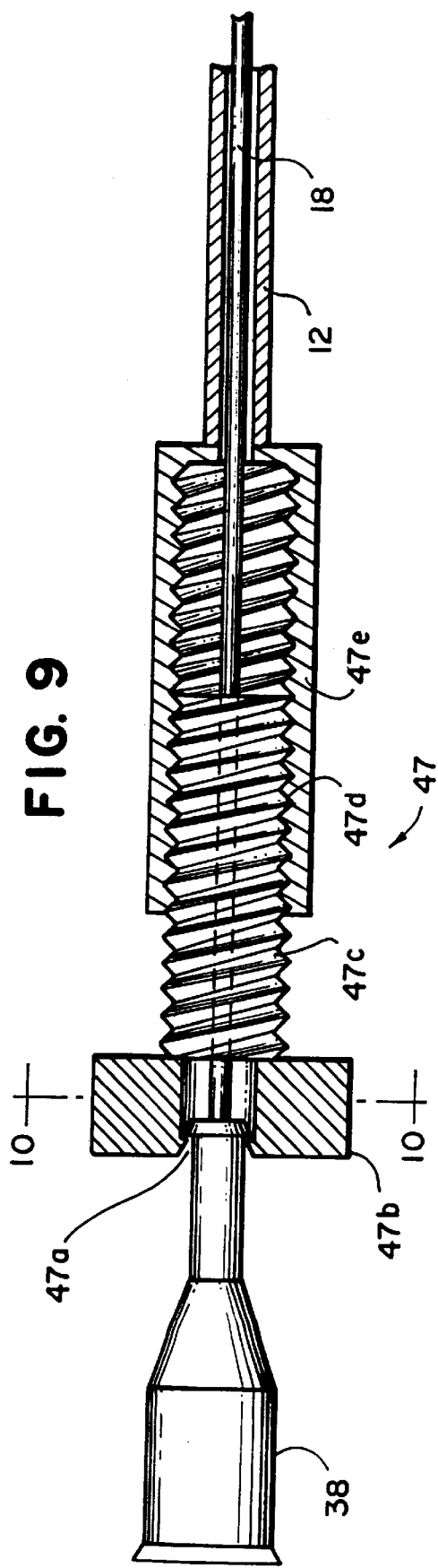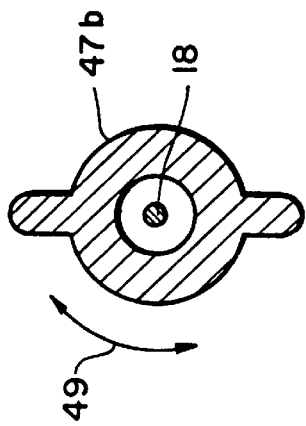

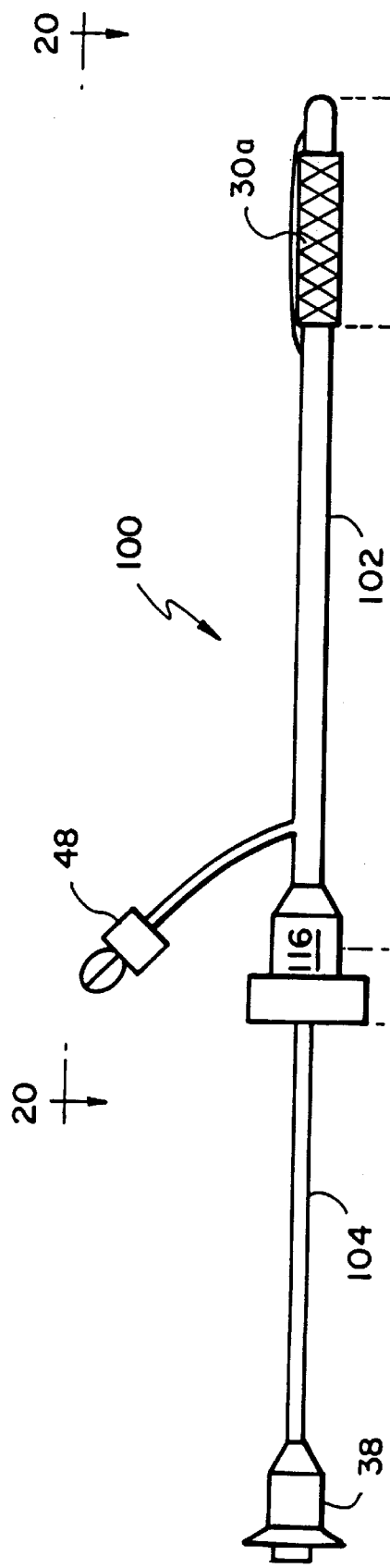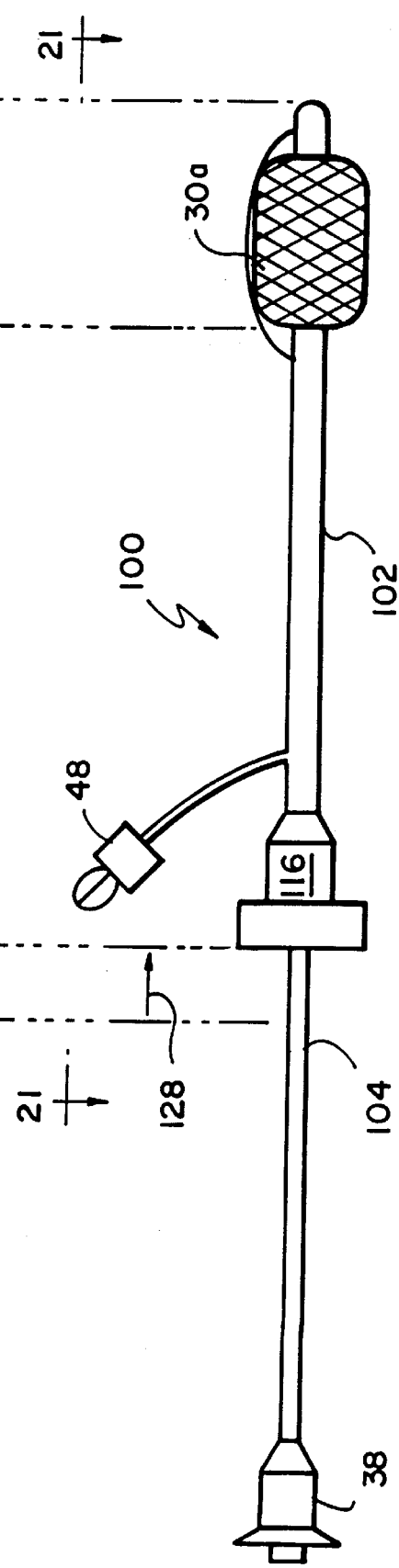

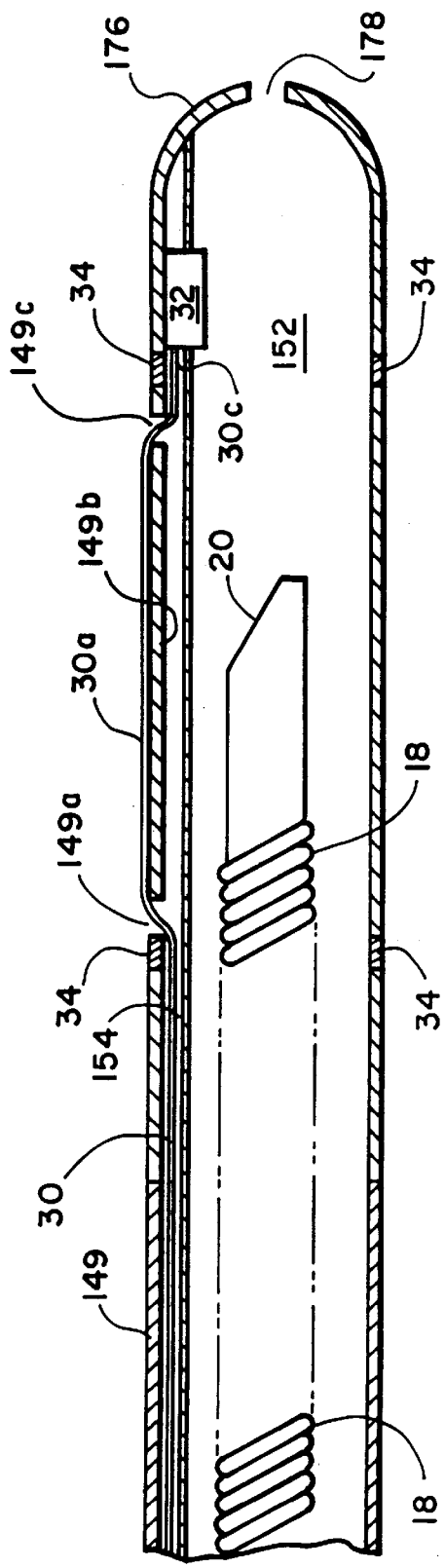
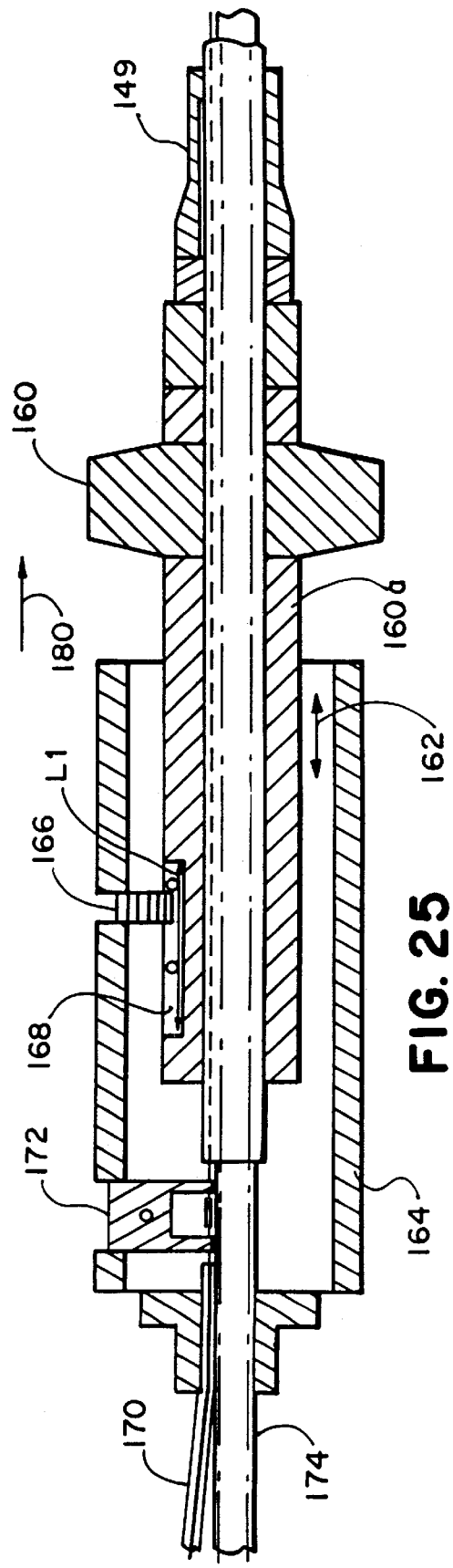
FIG. 24
FIG. 25

ULTRASOUND IMAGING CATHETER WITH A CUTTING ELEMENT

This is a continuation of co-pending PCT Application Ser. No. PCT/US96/11139, filed on Jul. 1, 1995, designating the U.S., which is a continuation-in-part of application Ser. No. 08/497,465, filed on Jun. 30, 1995, the entire disclosures of which are hereby incorporated herein by reference and now abandoned.

BACKGROUND

This invention relates to an ultrasound imaging catheter with a cutting element.

Often, a stricture, e.g., a stenosis, occlusion, or concentric scarring, caused by, for example, a tumor or a ureter in-growth may form in the wall of a vessel within the body of a living being. These strictures may be soft (e.g., tissue) or hard (e.g., plaque or a calcified region). A balloon dilatation catheter may be used to dilate and break apart the stricture. Often, however, the portion of the vessel wall containing the stricture reforms back to its narrow structure soon after dilatation. It was found that if the stricture was cut with, for example, a cold knife or a cauterizing cutter and a stent was placed in the opening of the cut, the stricture would heal around the stent in an enlarged diameter.

When a stricture is removed (e.g., cut, scored, broken apart, or chipped apart), a risk exists that a crossing vessel (i.e., a large blood vessel, for example, an impinging artery) may be located behind the stricture and simultaneously severed. Severing a crossing vessel may result in uncontrollable bleeding and dangerous blood loss. Several methods exist for determining the presence of crossing vessels, including: examining arteries by X-ray after the injection of radiopaque dyes (i.e., arteriography); examining the interior of a vessel wall with an endoscope to visually detect pulsations caused by an adjacent crossing vessel; and examining the tissue surrounding a vessel stricture with an ultrasound probe (i.e., endoluminal sonography). Generally, in endoluminal sonography, the ultrasound probe is inserted within the vessel to examine the stricture, the ultrasound probe is then removed, and if no crossing vessel was detected, a stricture removal device, e.g., cold knife or cauterize cutter, is inserted to carry out the longitudinal cutting of the structure.

SUMMARY

In one aspect, the invention features a catheter having a catheter body of extended length for insertion within a body of a living being. The catheter also includes an ultrasound imaging device disposed within a distal portion of the catheter body. The ultrasound imaging device generates electrical signals used by an ultrasound imaging system to display a real-time image of tissue surrounding the distal portion of the catheter. The catheter further includes a cutting element, e.g., an electrode wire or a laser fiber, having a proximal portion disposed within the catheter body. The catheter also includes a mechanism connected to the catheter body that causes the distal portion of the cutting element to extend from the catheter body. The distal portion of the cutting element generates energy in tissue with which it is brought in proximity to form a cut in the tissue. The ultrasound imaging device is positioned relative to the cutting element such that the real-time image produced by the ultrasound imaging system can include the cutting element in relation to the tissue.

Because the catheter includes both an ultrasound imaging device and an electrode wire or laser fiber, the number of catheter exchanges in certain procedures may be reduced, which may decrease the time in surgery. The ultrasound imaging device allows the physician to examine tissue, for example, behind a vessel stricture to determine if any crossing vessels are present, and the ultrasound imaging device may be used to accurately position, for example, the electrode wire to provide a cut in a precise location of the vessel stricture. Furthermore, the physician may use the ultrasound imaging device to monitor the action of the electrode wire in real-time by imaging the actual point of contact between the wire itself and the stricture to precisely determine the extent of the cut in the vessel stricture. This is especially important where the depth of cut must remain small, for example, to avoid severing a crossing vessel in the vicinity of a vessel stricture. Because the ultrasound imaging device can image the tissue surrounding the catheter, complications from blood loss may be reduced by preventing crossing vessels from being severed, and because time in surgery may be reduced where fewer catheter exchanges are required, patient trauma can also be reduced. Moreover, the use of ultrasound imaging may reduce a patient's exposure to the x-rays or radiation used in other procedures. The catheter may also be constructed for use with a variety of existing surgical devices and can be easily manufactured.

In another aspect, the invention features a catheter that includes an axial translation device mechanically coupled with the ultrasound imaging device. The translation device permits longitudinal movement of the ultrasound imaging device with respect to the catheter body, which permits relative movement between the ultrasound imaging device and the distal portion of the cutting element.

Because the ultrasound imaging device is movable along the length of the catheter body and in relation to, for example, an electrode wire or a laser fiber, the ultrasound imaging system can construct a series of two-dimensional images or a three-dimensional image of the tissue surrounding the catheter body-and can allow a physician to view the location of the cut from various positions.

Additional advantages and features are apparent from the following.

DETAILED DESCRIPTION

FIGS. 1 and 2 are side views of a catheter.

FIG. 3 is an enlarged side view of a distal portion of the catheter of FIG. 2.

FIGS. 4–6 are enlarged cross-sectional end views of the distal portion of the catheter of FIG. 3.

FIG. 7 is an enlarged cross-sectional side view of a cone coupler and a motor coupler of the catheter of FIGS. 1 and 2.

FIG. 8 is an enlarged, partial cross-sectional side view of a coaxial handle, a syringe, and a banana plug of the catheter of FIG. 1.

FIG. 9 is a cross-sectional side view of a coaxial, threaded handle.

FIG. 10 is a cross-sectional end view of the coaxial, threaded handle of FIG. 9.

FIGS. 18 and 19 are side views of a catheter.

Figure 20:
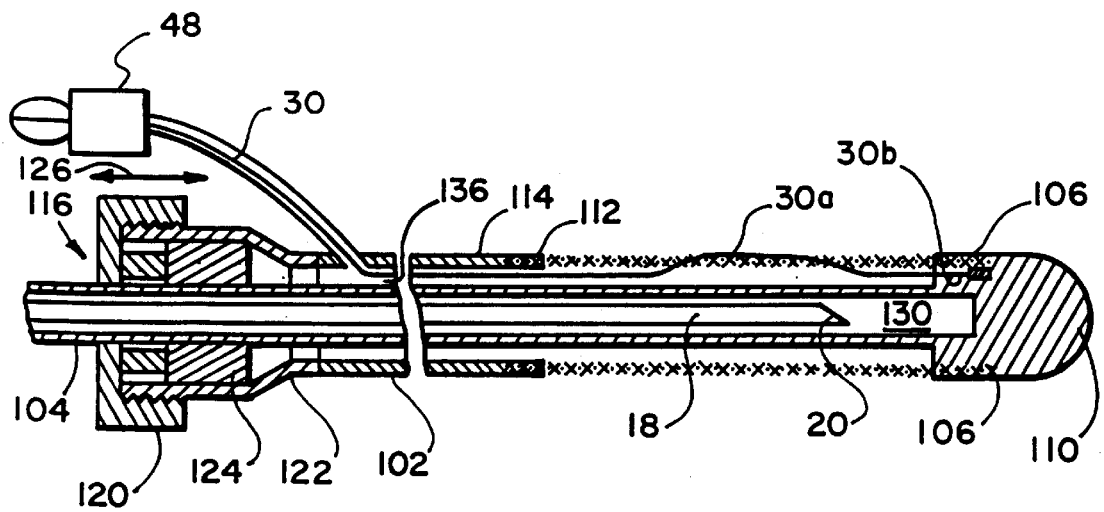
Figure 21:
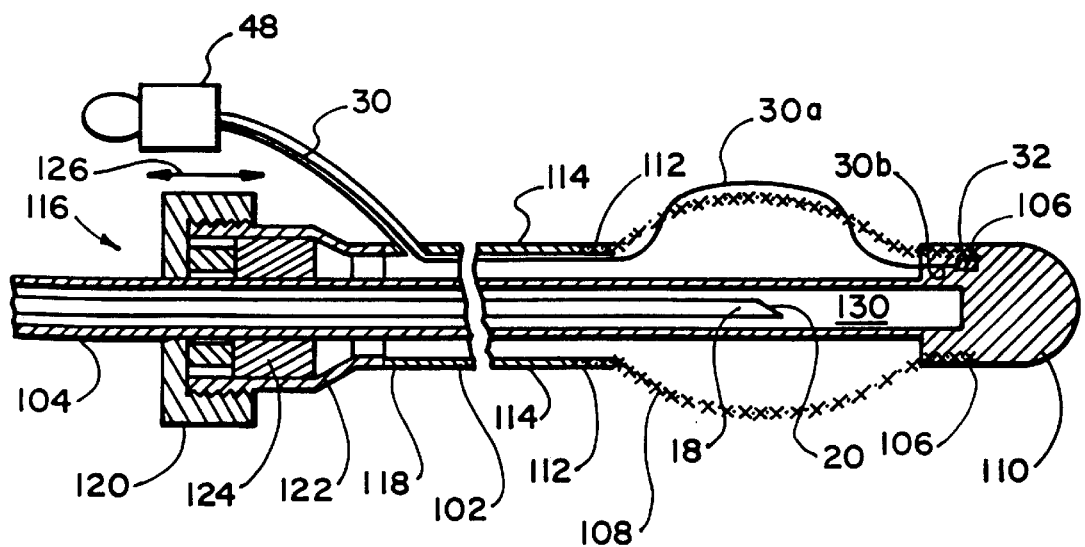

FIGS. 20 and 21 enlarged side views of a distal portion of the catheter of FIGS. 18 and 19, respectively.

Figure 22:
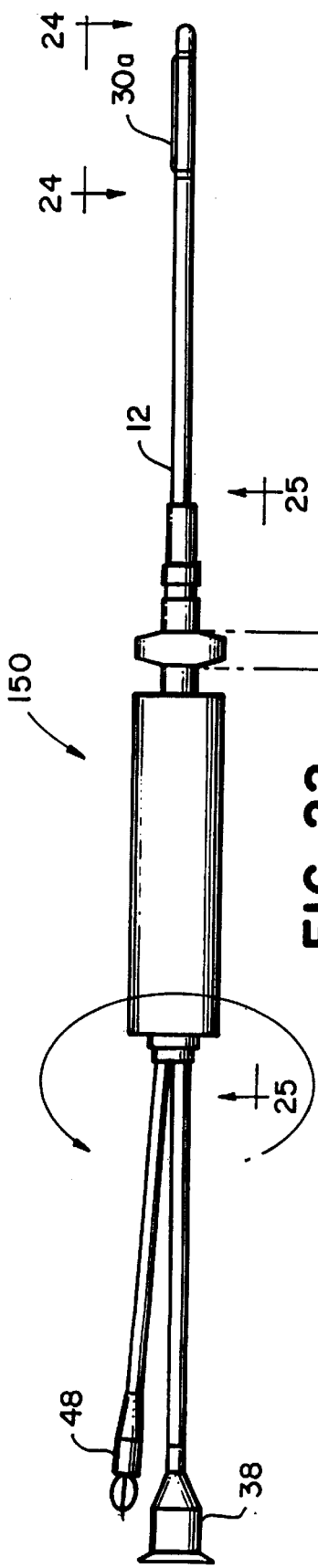
Figure 23:
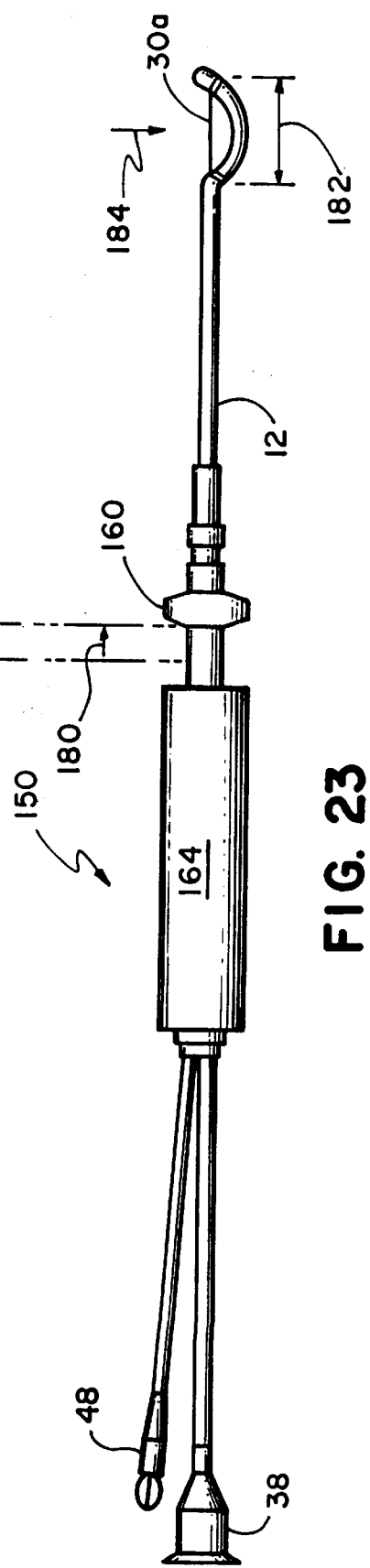

FIGS. 22 and 23 are side views of a catheter.

FIG. 24 is an enlarged cross-sectional side view of a distal portion of the catheter of FIG. 22.

FIG. 25 is an enlarged cross-sectional side view of a coaxial handle of the catheter of FIGS. 22 and 23.

Figure 26:
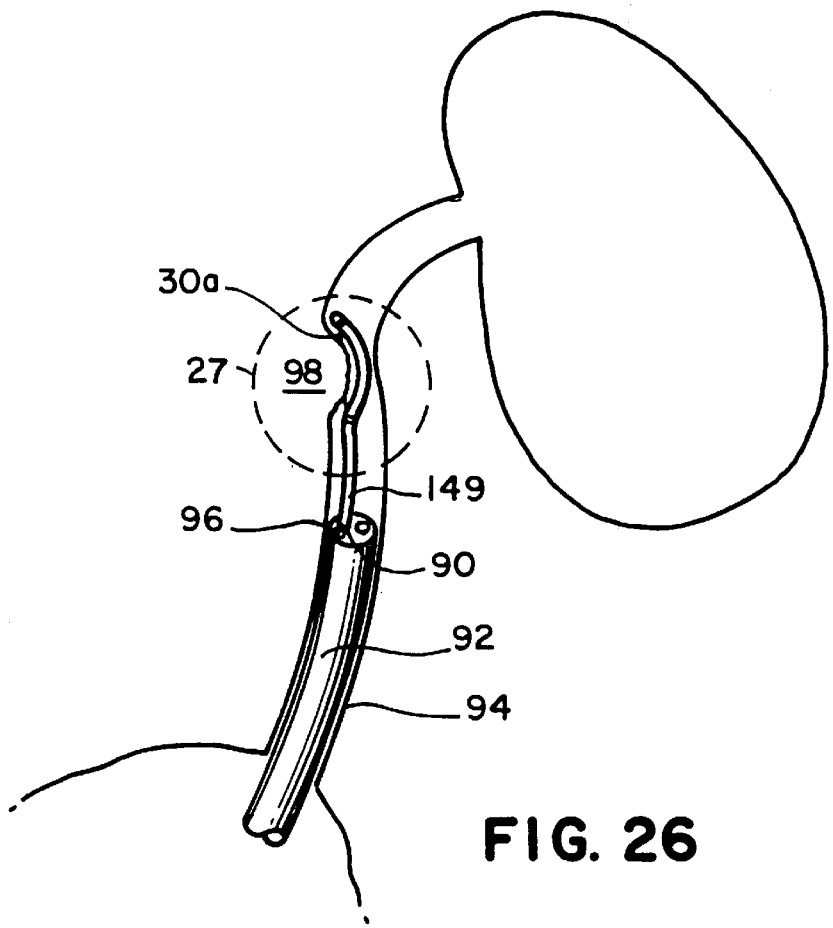
Figure 27:
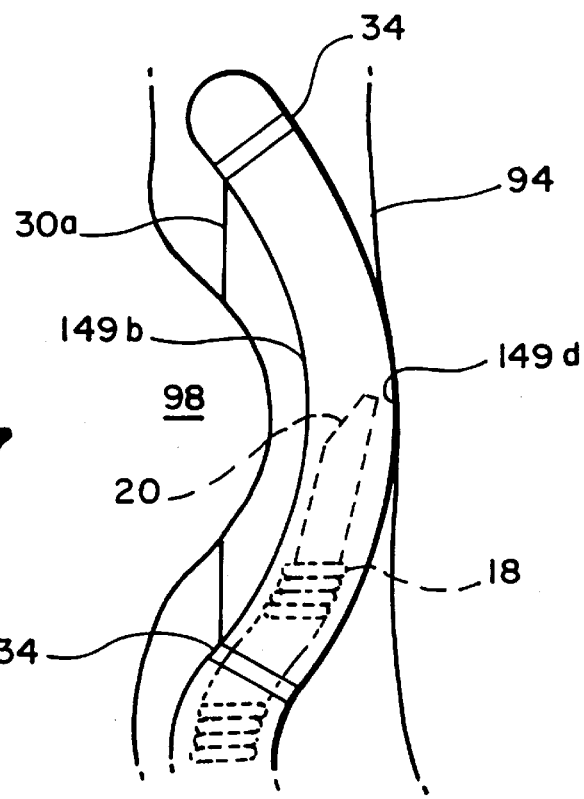

FIGS. 26–27 are cross-sectional side views illustrating use of the catheter of FIGS. 22 and 23.

Figure 28:
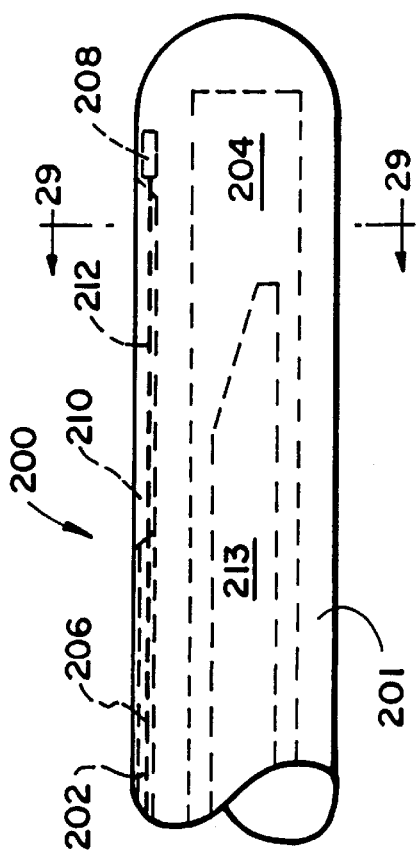
Figure 30:
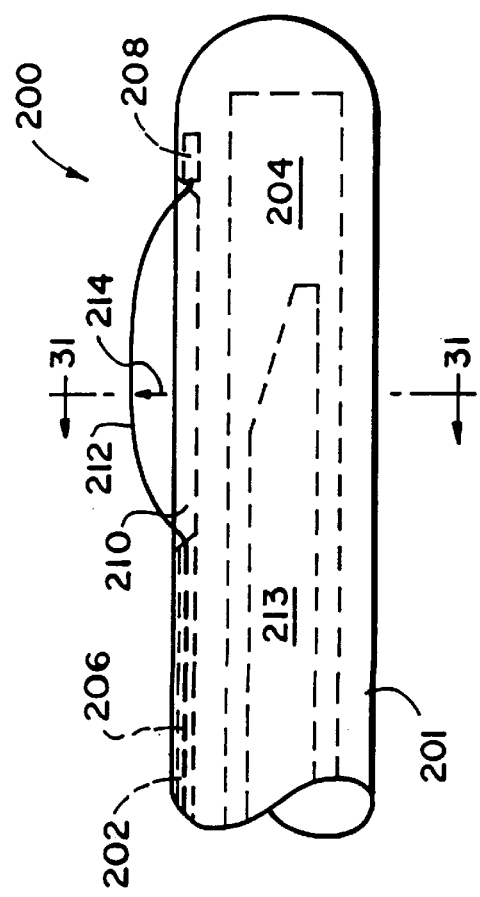

FIGS. 28 and 30 are side views of a distal portion of a catheter.

Figure 29:
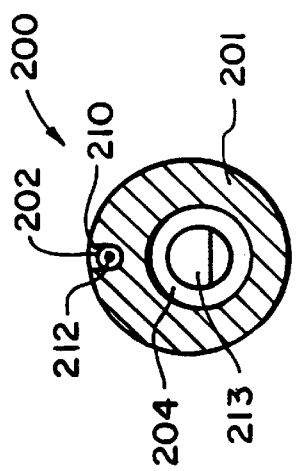
Figure 31:
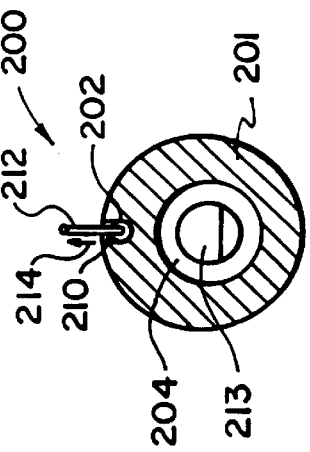

FIGS. 29 and 31 are end views of the catheter of FIGS. 28 and 30, respectively.

Figure 32:
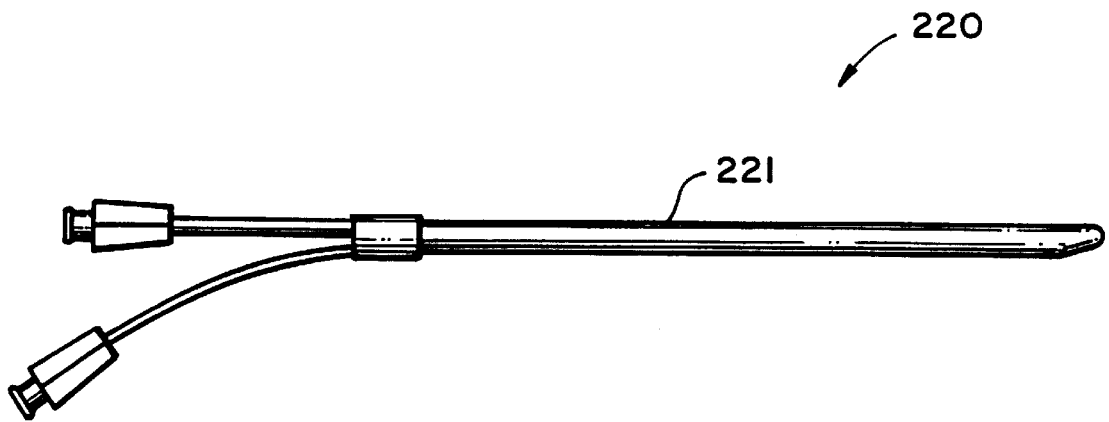
Figure 33:
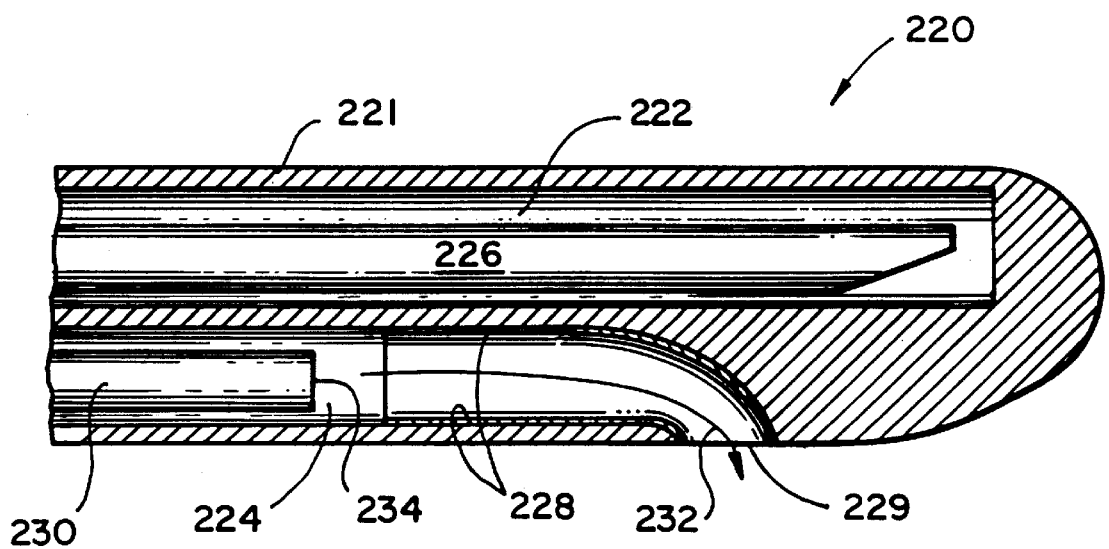
Figure 34:
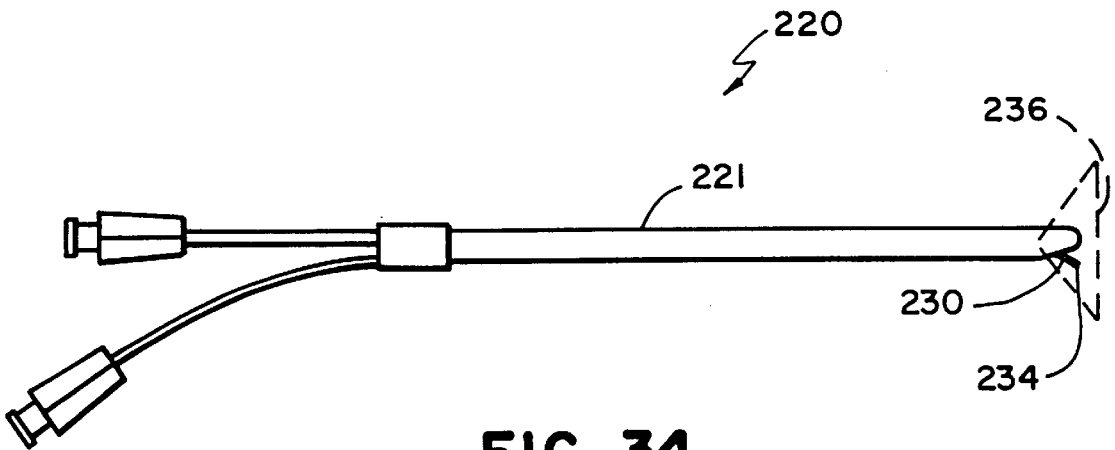

FIGS. 32, 33, and 34 are side views, with FIG. 33 being a cross-sectional side view, of a catheter.

Figure 35:
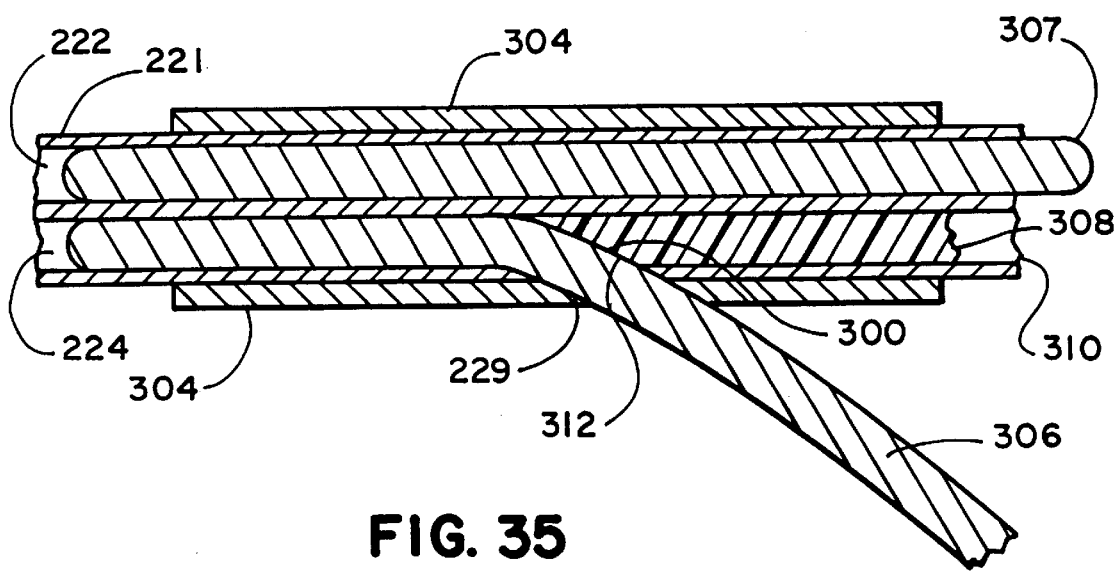

FIG. 35 is a cross-sectional side view of a distal portion of a catheter.

Figure 36:
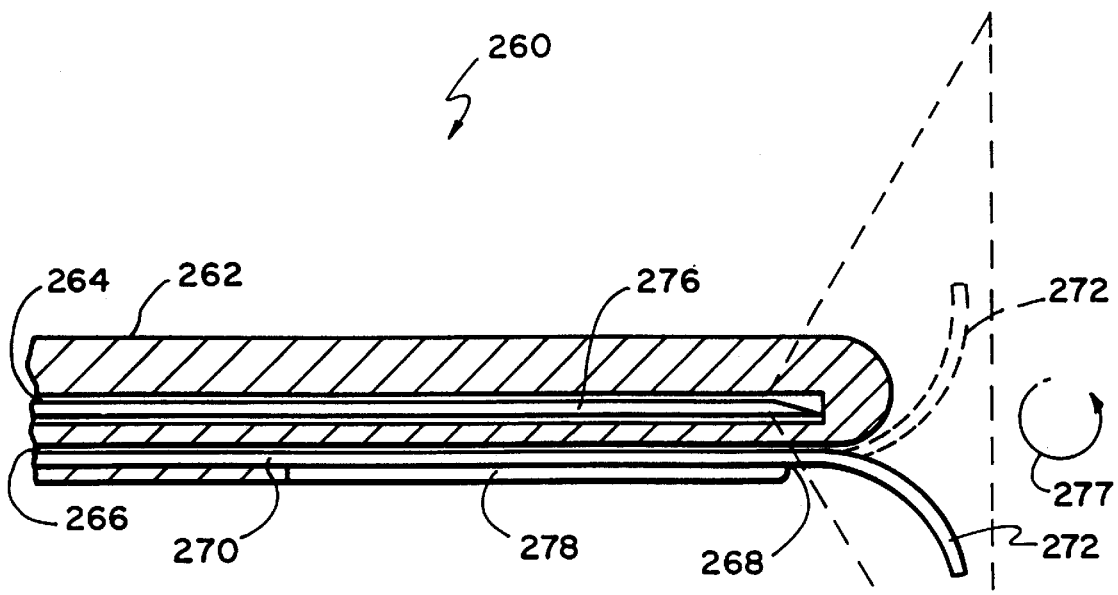
Figure 37:
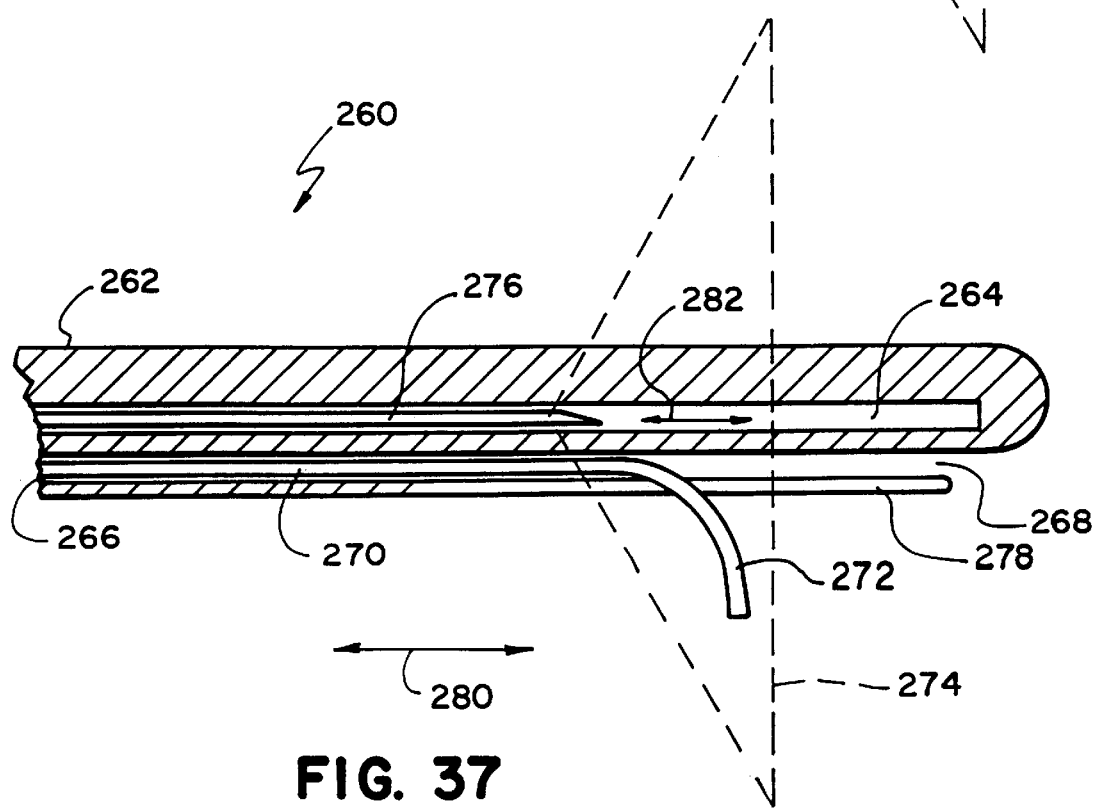

FIGS. 36 and 37 are cross-sectional side views of a distal portion of a catheter.

Figure 38:
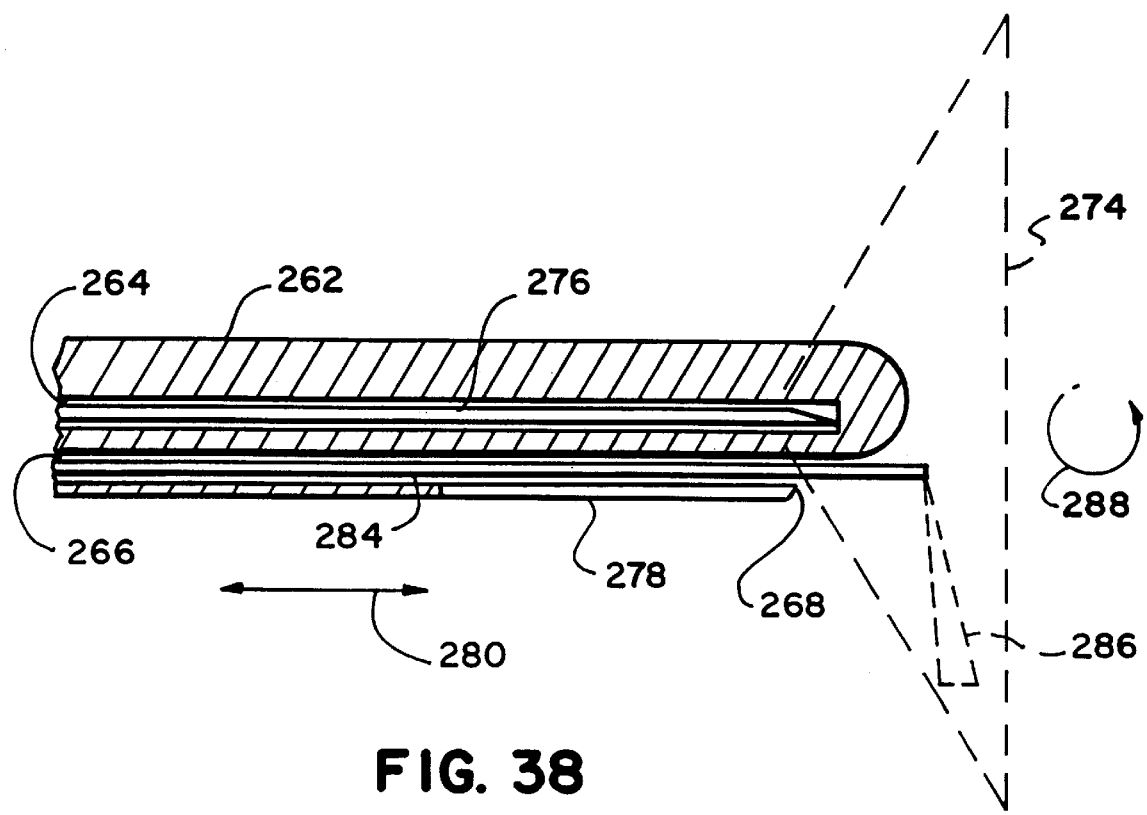

FIG. 38 is a cross-sectional side view of a distal portion of a catheter.

FIG. 39 is a side view of a distal portion of a balloon catheter having an electrode wire and a silicone sleeve surrounding the balloon for insulating the electrode wire from conductive liquids.

FIG. 40 is a cross-sectional view of the silicone sleeve of the catheter of FIG. 39.

FIG. 41 is a side view of a distal portion of another balloon catheter having an electrode wire and a silicone balloon sleeve.

FIG. 42 is a cross-sectional view of the silicone sleeve of the catheter of FIG. 41.

FIG. 43 is a side view of a distal portion of another balloon catheter having an electrode wire and a silicone balloon sleeve.

FIG. 44 is a cross-sectional view of the silicone sleeve of the catheter of FIG. 43.

FIG. 45 is a drawing of the distal end of one embodiment of the electrode wire of the balloon catheter of FIG. 43.

FIG. 46 is a side view of a distal portion of another. balloon catheter having an electrode wire and a silicone balloon sleeve.

FIG. 47 is a side view of a distal portion of a balloon catheter having a partially insulated electrode wire and a partial silicone cover on the balloon.

FIG. 48 is a side view of a distal portion of a catheter having a balloon mounted on one side of the catheter shaft and an electrode wire exposed on the other side of the catheter shaft.

STRUCTURE

Referring to FIGS. 1–6, a catheter 10 includes a flexible catheter body 12 and a dilatation balloon 14 disposed on a distal portion of catheter body 12. Catheter body 12 includes a central lumen 16 within which an ultrasound imaging device having a drive shaft 18 and an acoustic transducer 20 is disposed. Catheter body 12 also includes a balloon lumen 22 that is connected to a syringe 24. When a plunger 24a of syringe 24 is depressed (arrow 26, FIG. 2), fluid, preferably sonolucent saline, is forced through balloon lumen 22 and into balloon 14 to inflate balloon 14. A pressure gauge 24b is used to insure that balloon 14 is not over inflated.

Catheter body 12 further includes a wire lumen 28 within which a radio frequency (RF) cutting wire 30 (i.e., an electrode wire) is disposed. A distal portion 30a of the RF cutting wire extends through a first catheter body aperture 12a, along a portion 14a of the external surface of balloon 14, and through a second catheter body aperture 12c. A distal end 30b of the RF cutting wire is soldered to a metal hypo tube 32 around which plastic is first melted and then cured to fix metal hypo tube 32 to catheter body 12. Radiopaque markers 34 are disposed within catheter body 12 adjacent to each catheter body aperture 12a and 12c to mark the location of external portion 30a of the RF cutting wire.

Referring also to FIG. 7, drive shaft 18 of the imaging device passes through an insulation tube 36 to a cone coupler 38. Within cone coupler 38, drive shaft 18 is mechanically coupled to a motor (not shown) through a motor coupler 40. Motor coupler 40 permits the motor to rotate (arrow 42, FIGS. 3 and 7) drive shaft 18, and, hence, transducer 20. Within cone coupler 38, wires (not shown) that are electrically connected to transducer 20 and disposed within drive shaft 18 are electrically connected (not shown) to an ultrasound monitor (not shown) of the kind manufactured by Diasonics IVUS, Milpitas, Calif., and an ultrasound generator (not shown).

Referring to FIG. 8, drive shaft 18 and, hence, transducer 20, are axially translatable, (i.e., arrow 44) within catheter body 12 through the use of thumb control 46 (FIGS. 1 and 2). A physician places his/her thumb on thumb control 46 and pushes and pulls thumb control forward and backward (right and left, respectively, in the figure) to slide transducer 20 within catheter body 12. Referring to FIGS. 9 and 10, thumb control 46 may be replaced by a coaxial, threaded handle 47 that has a snap fit connector 47a for connecting to cone coupler 38. A physician can turn knob 47b clockwise or counter-clock wise (arrow 49) to rotate male threads 47c within female threads 47d of housing 47e to move transducer 20 within catheter body 12. Both the thumb control and the coaxial threaded handle may be hand actuated or controlled by an automatic translator means (not shown) to move transducer 20 along the length of catheter body 12. Details of various methods of enabling transducers to move in a longitudinal direction within a catheter body are found in U.S. Ser. No. 08/086,523, filed Jul. 1, 1993, and entitled, "CATHETERS FOR IMAGING, SENSING ELECTRICAL POTENTIALS, AND ABLATING TISSUE", the entire disclosure of which is hereby incorporated herein by reference.

Figure 11:
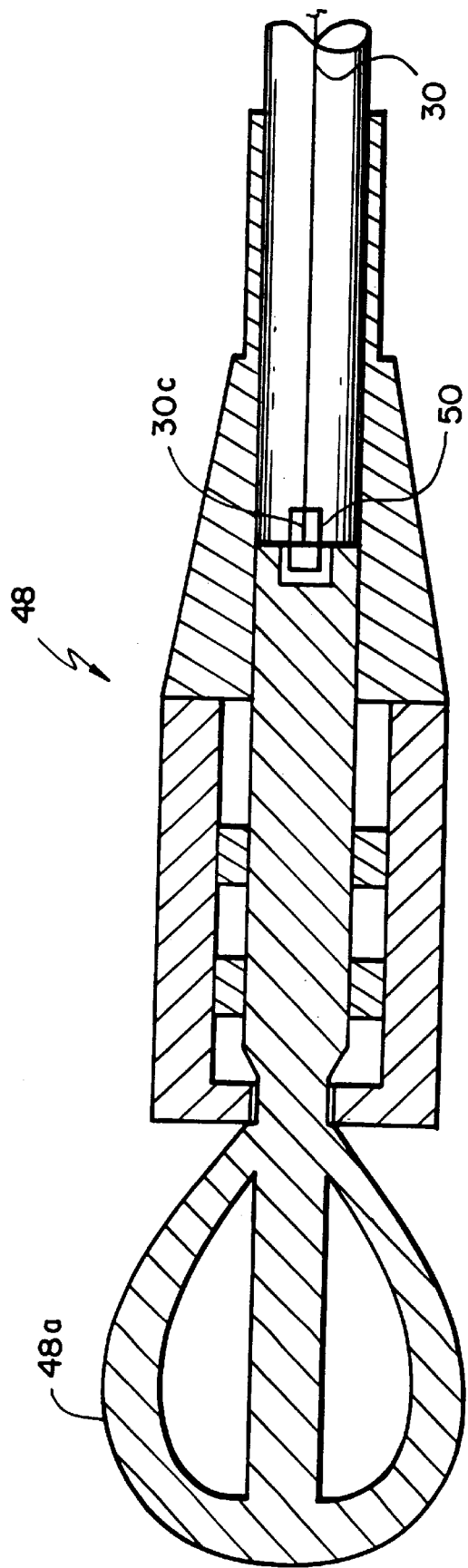
FIG. 11 is an enlarged cross-sectional side view of a banana plug of the catheter of FIGS. 1 and 2.

Referring also to FIG. 11, cutting wire 30 extends through catheter body 12 to a banana plug 48. Within banana plug 48, a proximal portion 30c of cutting wire 30 is soldered to a second metal hypo tube 50 that is electrically and mechanically connected to banana plug 48. A proximal portion 48a of banana plug 48 is electrically connected, and, hence, cutting wire 30 is electrically connected, to an RF generator (not shown).

Catheter body 12 has, for example, an outer diameter, D (FIG. 3), of about 6–10F and a length, L2 (FIG. 1), of about 30–100 cm. The length of catheter body 12 is divided into three portions, a stiff portion 52 of, for example, braided polymer between two polyethylene tubes, a sonolucent portion 54 of, for example, polyethylene, through which transducer 20 can efficiently transfer acoustic energy when provided power by the ultrasound generator, and a distal portion 56 which may consist of either braided polymer, polyethylene, or another material. The length, L1 (FIG. 3) of sonolucent portion 54 is, for example, 1–15 cm. Stiff portion 52 provides accurate torque transmission to allow catheter body 12 to be inserted along a tortuous path within a vessel of the body of a living being, and because radiopaque markers 34 are easily seen radiographically, the distal portion of the catheter can be roughly positioned within the body of a living being through X-ray fluoroscopy. Alternatively, the catheter can be positioned with a guide wire, through an endoscope, or through the use of ultrasound.

Central lumen 16 of catheter body 12 and the vessel within which catheter body 12 is inserted is filled with fluid (e.g., blood, water, saline) to allow the acoustic energy produced by transducer 20 to be efficiently transferred to the surrounding vessel and tissue. Where the vessel is, for example, the ureter, urine can provide the necessary acoustic coupling within the vessel. The catheter is filled with fluid by, for example, piercing the catheter body with a needle and injecting the fluid, within the catheter body. Saline is preferred due to its sonolucent properties.

Figure 13:
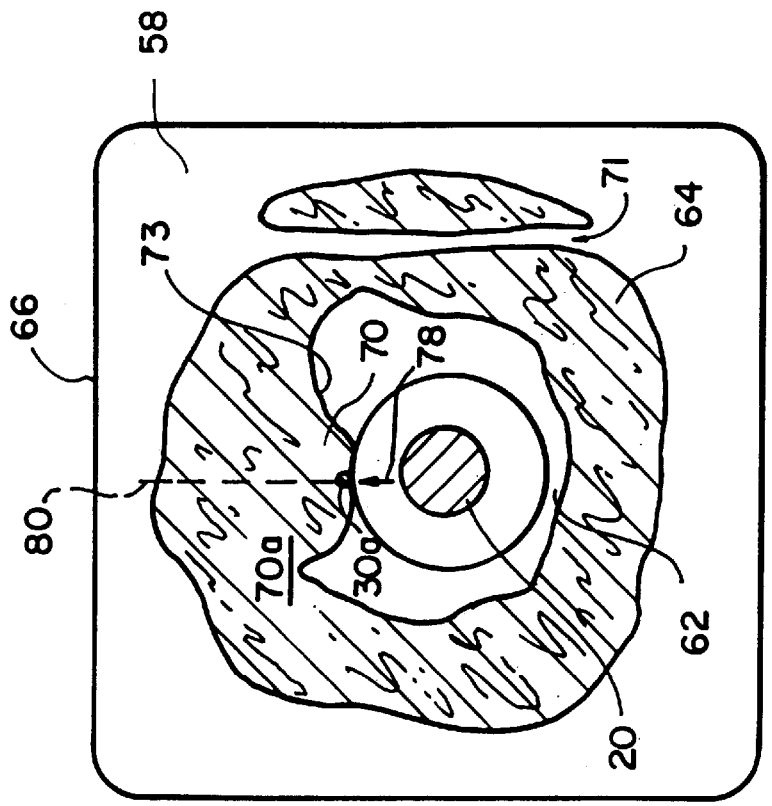
FIGS. 12–13 are plan views of the display of monographic images on an ultrasound monitor screen.
Figure 12:
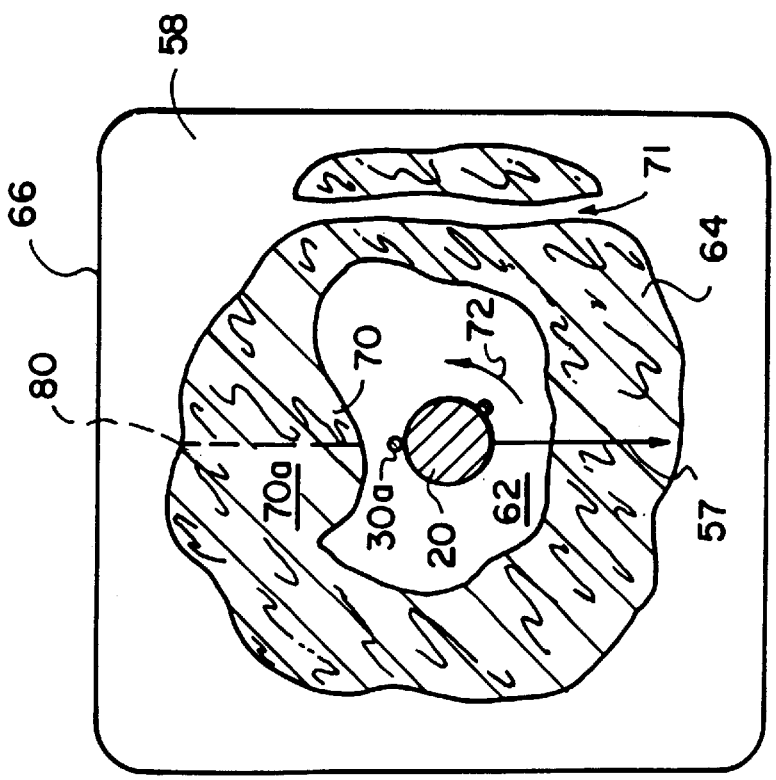

Referring to FIGS. 12 and 13, once positioned within the body of a living being, transducer 20 is driven in pulse echo mode (i.e., short acoustic pulses) from an ultrasound generator (not shown) at an average imaging power level of, for example, less than 1 Watt to produce acoustic energy at a frequency of approximately 12.5–20 Hz. Such a frequency provides an axial resolution of about 0.1 mm and a maximum tissue penetration (arrow 57) of about 1.5–2 cm. The beam angle produced by transducer 20 is typically less than 3°. The short pulse, narrow beam acoustic energy pattern provides high lateral and axial resolution. The motor (not shown) rotates (arrow 42, FIG. 3) drive shaft 18, and, hence, transducer 20, 360° (to provide a 360° sweep) at approximately 30 revolutions per minute to produce a real-time, cross-sectional monographic image 58 of a vessel 62 and a portion 64 of the tissue surrounding vessel 62 on a screen 66 of the ultrasound monitor. The image is at about 10° off from true perpendicular. Images displayed on a display screen of the ultrasound monitor (not shown) are built from reflections received from a sweep of the area to be imaged using the known angular position of the transducer and the range (distance) of the return reflections. Details of such an imaging transducer are found in U.S. Pat. No. 5,421,338, issued Jun. 6, 1995, and entitled, "ACOUSTIC IMAGING CATHETER AND THE LIKE," the entire disclosure of which is hereby incorporated herein by reference.

Figure 14:
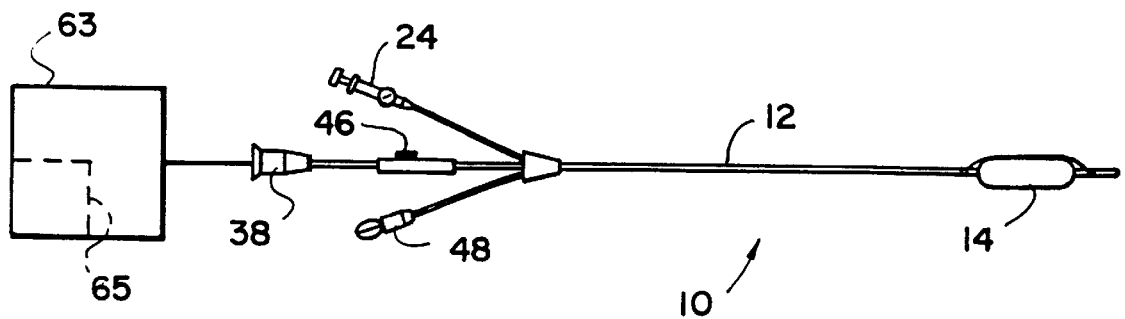
FIG. 14 is a plan view of the catheter of FIG. 1 connected to an ultrasound imaging system.
Figure 15:
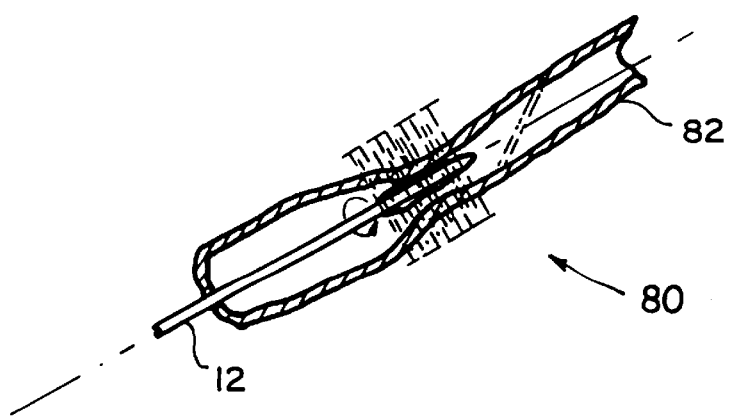
FIG. 15 is a perspective view of a three-dimensional monographic image.

Referring to FIG. 14, as thumb control 46 (FIGS. 1, 2, and 8) is used to axially slide transducer 20 within catheter body 12, periodically an ultrasound monitor 63 stores images produced by the transducer. A computer 65, within (or connected to) the ultrasound monitor, then compiles these stored images in accordance with their relative positions to produce either a series of two-dimensional images 58 (FIGS. 12 and 13) or a three-dimensional image 80 (FIG. 15), on the ultrasound monitor's display, of the tissue 82 surrounding the catheter body. Such a series of two-dimensional images or a three-dimensional image may give the physician a better understanding of the size and structure of a vessel stricture. Details of such an imaging transducer are found in U.S. Pat. No. 5,421,338, issued Jun. 6, 1995, entitled "ACOUSTIC IMAGING CATHETER AND THE LIKE," and in U.S. Ser. No. 08/086,523, filed Jul. 1, 1993, and entitled "CATHETERS FOR IMAGING, SENSING ELECTRICAL POTENTIALS, AND ABLATING TISSUE."

Referring again to FIGS. 12 and 13, the contrast in image 58 indicates the density of the surrounding material, and through image 58 a physician can determine the presence of any vessel strictures, for example, vessel stricture 70, and any crossing vessels, for example, crossing vessel 71 (contrast indicates a lack of density, i.e., an opening or vessel) located in the cross-section of vessel 62 and tissue 64 surrounding transducer 20. If no stricture is imaged, catheter 10 can be pushed or pulled to slide transducer 20 and catheter body 12 along vessel 62 and/or thumb control 46 can be pushed or pulled to slide transducer 20 within catheter body 12 until image 58 indicates that transducer 20 is located adjacent to a vessel stricture.

After positioning transducer 20 adjacent to vessel stricture 70, if no crossing vessel is detected in the tissue 70a behind vessel stricture 70, catheter 10 is rotated (arrow 72, FIGS. 1 and 12) to locate external portion 30b of cutting wire 30 adjacent to vessel stricture 70. Stiff portion 52 of catheter body 12 transfers the torque from the rotation of catheter 10 to catheter body 12 to rotate distal portions 54 and 56 of catheter body 12.

Referring also to FIGS. 1 and 2, as plunger 24a of syringe 24 is depressed, fluid is forced into the balloon lumen and then into the balloon to inflate (arrow 78, FIG. 13) the balloon. Inflation of the balloon brings the external portion 30a of the cutting wire in proximity to vessel stricture 70. When contact is made (or before contact is made), the RF generator (not shown) attached to banana plug 48 is activated and supplies RF energy to cutting wire 30. Prior to insertion of catheter body 12, the living being is placed on a grounding pad. As a result, when RF energy is applied to cutting wire 30, external portion 30a performs as a monopolar electrode and when brought in proximity to vessel stricture 70, current passes through vessel stricture 70 and heats the tissue or material (e.g., plaque) immediately adjacent cutting wire 30a. The heat is sufficient to denature or ablate the tissue cells or plaque immediately adjacent external portion 30a to cause the stricture to be cut (dashed line 80) and to cause small blood vessels to be simultaneously cauterized.

The application of RF energy to the cutting wire may interfere with ultrasound imaging by the transducer. If so, the power applied to the cutting wire and the power applied to the imaging device is cycled so that power is applied to one or the other but not both simultaneously.

Using image 58, which displays the wire itself in relation to the stricture, a physician can make real-time evaluations regarding the location and the depth of the cut. Prior to applying power to the cutting wire, the physician can insure that external portion 30a is in proximity to a precise portion, for example, the center, of stricture 70 and not some other point, for example, side 73 of the stricture. After contact is made and power is applied to the cutting wire for a period of time, for example, 3 seconds, the power is removed from the cutting wire and power is applied to the imaging device to allow the physician to observe the depth to which external portion 30a of cutting wire 30 extends within vessel stricture 70. Through this process of cutting and imaging the physician insures that an effective cut is created and prevents cutting vessel stricture 70 too deeply, for example, severing a crossing vessel 71 (FIG. 13).

Stiff portion 52, when consisting of braided polymer, shields the drive shaft and cutting wire. Cutting wire 30 may consist of, for example, nitinol or stainless steel, and may be round or flat with a thickness of, for example, approximately 0.010–0.020 inches.

The combination of cutting and dilating the vessel with balloon 14 causes the stricture to break apart and may eliminating the need for additional procedures. To prevent the stricture from re-forming, a stent may be placed within the opening.

Figure 16:
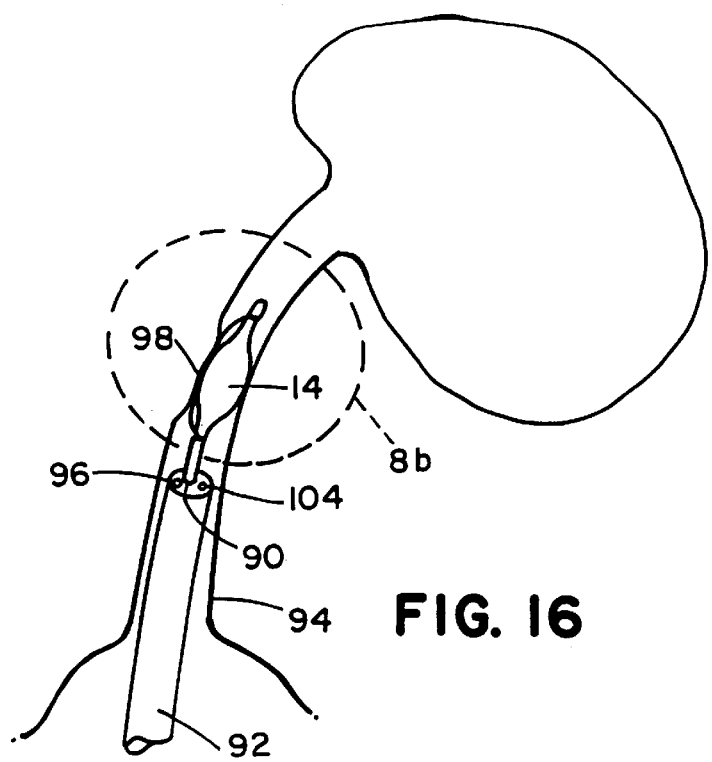
FIGS. 16–17 are cross-sectional side views illustrating use of the catheter of FIGS. 1 and 2.
Figure 17:
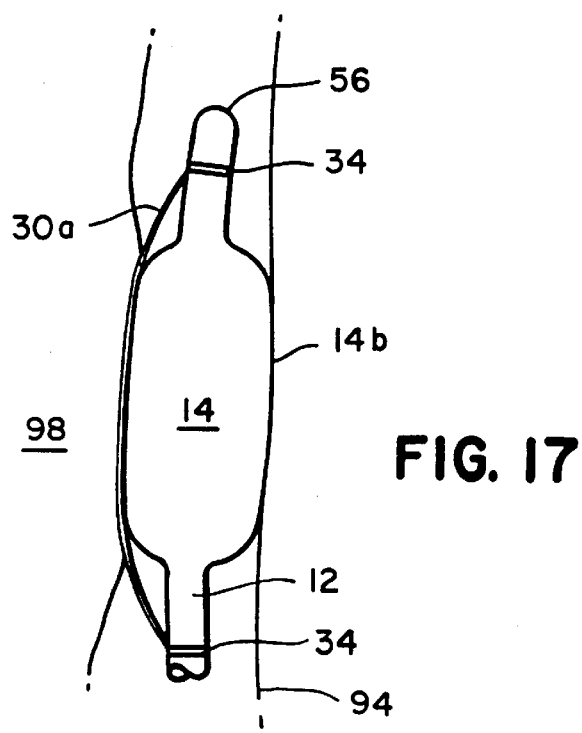

Referring to FIGS. 16–17, catheter body 12 of catheter 10 (FIG. 1) is inserted within a lumen 90 of an ureterscope 92 which is inserted within the ureter 94 of a living being. Radiopaque markers 34 are used to roughly position catheter body 12 within the body of a living being and an optical lens 96 within ureterscope 92 is used to visually locate a stricture 98 within ureter 94. An-ultrasound monitor then activates transducer 20 while a motor rotates drive shaft 18 and transducer 20 to produce a real-time cross-sectional monographic image of ureter 94 and the tissue surrounding ureter 94 on a display screen of the ultrasound monitor.

Multiple real-time cross-sectional monographic images are produced, by moving the transducer within the catheter body through the use of the thumb control, and examined to determine if any crossing vessels (not shown) are present in the tissue of vessel stricture 98 or in the tissue 98a behind vessel stricture 98. If no crossing vessels are present, catheter 10 (FIG. 1) is rotated and the real-time monographic image is continually examined to position external portion 30a of the cutting wire accurately with respect to the vessel stricture.

Once external portion 30a is properly positioned, RF energy is applied to the cutting wire. The physician continues to inflate the balloon to increase the depth of the cut formed by the cutting wire. A side 14b of the balloon pushes against and is stabilized by the wall of ureter 94.

The physician then pulls back on plunger 24a to deflate the balloon and pulls back on catheter body 12 to remove catheter body 12 from the body of the living being.

OTHER EMBODIMENTS

Catheter body 12 may be inserted within the body of a living being in many ways, including: by passing catheter body 12 directly into the body; by passing catheter body 12 through an endoscope, a resectoscope, or a sonolucent sheath; or by providing a separate lumen for a guide wire and positioning catheter body 12 with the guide wire.

The above described catheters may be used for the treatment of a variety of problems, including UPJ obstruction, Ureteral strictures, and esophageal strictures.

Once a vessel stricture is removed, any stones which were unable to pass by the vessel stricture may be removed. Where the path through the body of the living being is relatively straight (i.e., not tortuous), stiff portion 52 (FIG. 3) may be replaced with other less stiff material such as polyethylene.

Referring to FIGS. 18–21, a catheter 100 includes a flexible outer catheter body 102 and a flexible inner catheter body 104. A distal end 106 of a mesh dilatation balloon 108 is thermo bonded to a distal end 110 of inner catheter body 104, while a proximal end 112 of mesh balloon 108 is thermo bonded to a distal end 114 of outer catheter body 102. A touhy borst handle 116 is connected to a proximal end 118 of outer catheter body 102, while inner catheter body 104 passes through handle 116 and is, connected to cone coupler 38.

Handle 116 includes a cap 120, a body 122, and a grommet 124. Tightening cap 120 compresses grommet 124 axially which reduces its diameter causing it to lock onto inner catheter body 104. With cap 120 loose, handle 116 is free to slide (arrow 126) axially along inner catheter body 104. As shown in FIGS. 19 and 21, advancing (arrow 128) handle 116 along inner catheter body 104 causes the material (e.g., polyester) of mesh balloon 108 to push together and lift away from catheter 10.

Inner catheter body 104 includes a central lumen 130 (FIGS. 20–21) within which an ultrasound imaging device having a drive shaft 18 and an acoustic transducer 20 is disposed. Outer catheter body 102 includes a wire lumen 136 within which an RF cutting-wire 30 is disposed. An external portion 30a of the RF cutting wire extends outwardly through a proximal portion of the mesh balloon and inwardly through a distal portion of the mesh balloon. A distal end 30b of the RF cutting wire is soldered to a metal hypo tube 32 around which plastic is first melted and then cured to fix metal hypo tube 32 to the distal end of the inner catheter body. As the mesh balloon expands, it raises external portion 30a of the RF cutting wire, and as described above, once in contact with tissue, power may be applied to the cutting wire to cut the tissue adjacent to the external portion 30a.

Because a mesh dilatation balloon is not inflated by filling it with liquid, there is no danger that the balloon may rupture within a patient. Catheters having dilatation balloons (FIGS. 1 and 18) simultaneously cut and break apart (dilate) vessel strictures. The symmetrical/cylindrical shape of the balloons apply even force across the length of vessel strictures. Where a cut without dilatation is required, a catheter of the type shown in FIGS. 22–23 may be used.

Referring to FIGS. 22–24, a catheter 150 includes a flexible catheter body 149. Catheter body 149 includes a central lumen 152 within which an ultrasound imaging device having a drive shaft 18 and an acoustic transducer 20 is disposed. Catheter body 149 also includes a wire lumen 154 within which an RF cutting wire 30 is disposed. An external portion 30a of RF cutting wire 30 extends through a first catheter body aperture 149a, along a portion 149b of the external surface of catheter body 149, and through a second catheter body aperture 149c. The distal end 30b of RF cutting wire 30 is soldered to a metal hypo tube 32 around which plastic is first melted and then cured to fix metal hypo tube 32 to catheter body 149. Radiopaque markers 34 are disposed within catheter body 149 adjacent to each catheter body aperture 149a, and 149c to mark the location of external portion 30a of RF cutting wire 30.

Referring also to FIG. 25, catheter body 149 extends within and is attached to (i.e., does not slide within) a push hub 160 with, for example, a luer fitting or as a single piece joint. A portion 160a of push hub 160 extends within and slides (arrow 162) within a coaxial handle 164. A set screw 166 mounted to coaxial handle 164 rests within a groove 166 of a portion 160a of push hub 160. The length, L1, of groove 168 establishes the distance push hub 160 may slide within coaxial handle 164, and the combination of set screw 166 and groove 168 prevents independent rotation of push hub 160 and coaxial handle 168 (i.e., rotation of catheter 150 rotates both hub 160 and coaxial handle 164 together).

Cutting wire 30 extends through catheter body 149, push hub 160, coaxial handle 164, and an insulating tube 170 to a banana plug 48. Within coaxial handle 164, a portion 30d of cutting wire 30 is attached to coaxial handle 164 with a set screw 172 such that cutting wire 30 does not slide within coaxial handle 164.

Drive shaft 18 of the imaging device passes through push hub 160, coaxial handle 164, and an insulation tube 174 to a cone coupler 38.

As mentioned above, the central lumen of the catheter body and the vessel within which the catheter body is inserted is filled with fluid in order for acoustic energy produced by the transducer to be efficiently transferred to the surrounding vessel and tissue. Catheter body 149 can have a closed or opened distal portion 176. Where the distal portion of the catheter has an opening 178 (FIG. 24) urine or other fluid in the vessel can flow into the catheter body and provide the necessary acoustic coupling within the catheter body. Additionally, a pump (not shown) may be connected to the catheter body to pump fluid through the catheter body and out opening 178. The passing fluid may transfer heat away from, and thereby cool, the transducer.

Referring again to FIGS. 22, 23, and 25, by grasping axial handle 164 with one hand and push hub 160 with the thumb of that hand, a physician may push (arrow 180, FIGS. 23 and 25) push hub 160 distally while maintaining the position of handle 164. Because catheter body 149 is fixed to push hub 160, pushing push hub 160 also pushes catheter body 149 which would tend to extend distal portion 176 of catheter body 149 further within the body. However, because cutting wire 30 is fixed within handle 164 by set screw 172 and slides within push hub 164, distal end 30c of cutting wire 30 prevents catheter body 149 from advancing further and, when push hub is pushed, for example, 1–2 cm, distal portion 182 of catheter body 149 bends or bows (arrow 184, FIG. 23).

Referring to FIGS. 26–27, the catheter body 149 of a catheter 150 (FIG. 22) is inserted within a lumen 90 of an ureterscope 92 which is inserted within the ureter 94 of a living being. Radiopaque markers 34 are used to roughly position catheter body 149 within the body of a living being and an optical lens 96 within ureterscope 92 is used to visually locate a stricture 98 within ureter 94. An ultrasound monitor then activates transducer 20 while a motor rotates drive shaft 18, and hence, transducer 20, to produce a real-time cross-sectional monographic image of ureter 94 and the tissue surrounding ureter 94 on a display screen of the ultrasound monitor.

The real-time cross-sectional monographic image is examined to determine if any crossing vessels (not shown) are present in the tissue of vessel stricture 98 or in the tissue 98a behind vessel stricture 98. If no crossing vessels are present, catheter 150 is rotated and the real-time monographic image is continually examined to determine if external portion 30a of the cutting wire is properly positioned adjacent to stricture 98.

Once external portion 30a of the cutting wire is properly positioned, the physician holds coaxial handle 164 (FIGS. 22, 23, and 25) with one hand while pushing push hub 160 with the thumb of that hand to bend the distal portion of catheter body 149 and cause external portion 30a of the cutting wire to lift away from the external surface 149b of catheter body 149. A side 149d of the catheter body pushes against and is stabilized by the wall of ureter 94. RF energy is applied to cutting wire 30, and when external portion 30a is in proximity to (or contact with) stricture 98, stricture 98 is cut. The physician then pulls back on push hub 160 causing the distal portion of the catheter body to straighten and then pulls back simultaneously on push hub 160 and coaxial handle 164 to remove the catheter body from the body of the living being.

Instead of forming a cut (i.e., slice), external portion 30a of cutting wire 30 may be used to sweep through a vessel stricture to remove a portion or all of the vessel stricture. Once the distal portion of catheter body 149 is bent and RF energy is applied to cutting wire 30, catheter 150 can be rotated to cause external portion 30a to sweep from one side to the other side of stricture 98. In such a procedure, catheter body 149 should be inserted within an ureterscope or a resectoscope having a flushing lumen (not shown) through which portions of removed tissue or material may be flushed from the vessel.

Referring to FIGS. 28–31, a catheter 200 includes a catheter body 201 having a wire lumen 202 and a central lumen 204. An electrode wire 206 is disposed in the wire lumen, and the electrode wire's distal end is fixed in a hypo tube 208. The catheter body also includes a slot 210 into which the wire lumen opens leaving a portion 212 of the electrode wire in the slot exposed. The electrode wire's proximal end (not shown) is electrically connected to an RF generator while a mid-portion of the electrode wire is fixed to an axial translation device (not shown), e.g., thumb control 46 (FIGS. 1 and 2).

Once the catheter is in position within a patient and a physician has determined, through the use of an ultrasound transducer 213, that it is safe (e.g., no crossing-vessels) to cut the surrounding tissue (e.g., a vessel stricture), the physician manipulates the axial translation device to cause the wire to push against hypo tube 208 and extend (or lift, arrow 214) away from the catheter body. The transducer is then used to precisely place the extended electrode wire in proximity to the tissue and, as described above, RF energy is applied to the electrode wire to cut the vessel stricture.

The small profile of catheter 200 allows the catheter to be delivered into tight strictures where a balloon catheter may not fit even in its deflated state.

Referring to FIGS. 32–34, a catheter 220 includes a catheter body 221 having a central lumen 222 and a wire lumen 224. An ultrasound transducer 226 is disposed in the central lumen while a cutting element, e.g., an electrode wire 230 or laser fiber (not shown), is disposed in the wire lumen. A cylindrical hypo tube 228 is also disposed within the wire lumen by cutting an aperture 229 in the catheter body near the distal end of the wire lumen, inserting the hypo tube into the distal end of the wire lumen, and gluing or heat fixing the hypo tube to the catheter body. A proximal end the electrode wire is connected to an RF generator (not shown) and a mid-portion is connected to an axial translation device (not shown), as described above. By manipulating the axial translation device, the physician causes the wire to pass through (arrow 232) the hypo tube which is bent at an angle, e.g., 30–90°, and directs the electrode wire out of the catheter body (FIG. 34).

The wire extends, for example, approximately 6 mm away from, due to the bend of the hypo tube, the outside of the catheter body and has a diameter of, for example, 0.020". A wire of this diameter is sufficiently flexible to extend through the bend of the hypo tube and is sufficiently stiff to withstand pressure from surrounding tissue. Additionally, the electrode wire is strong enough to serve as a guide wire for introducing the catheter into a patient before RF energy is applied to the wire. Alternatively, a separate guide wire is used in conjunction with the wire lumen to place the catheter and the electrode wire is inserted within the wire lumen after placement.

Once the wire is in an extended position, RF energy is applied and the tip 234 of the wire is used to cut surrounding tissue or vessel strictures. The cut may be a minimum of a single point cut, or the catheter may be pushed or pulled to create a linear cut or rotated to create a circular cut. The depth of the cut depends on the length to which the electrode wire is extended from the catheter.

The distal portion of the catheter body is constructed of sonolucent material. Therefore, although the electrode wire extends away from the catheter body, it is still within the visualization range 236 of the transducer.

Alternatively, the electrode-wire is replaced with a laser fiber and laser energy emitted from the laser fiber is used to cut the tissue. The laser fiber need not be in contact with or close proximity to the tissue to be cut which avoids any "sticking" problems that may occur when tissue becomes attached to the cutting element. When tissue becomes attached to the cutting element and the cutting element is pulled away, the tissue may be torn and begin to bleed. Additionally, the laser energy emitted by the laser fiber provides less interference with the ultrasound imaging. As a result, the power to the laser fiber and the power to the transducer may not need to be cycled on and off to provide clear imaging while cutting.

Referring to FIG. 35, instead of inserting the hypo tube into the wire lumen, a ramp 300 may be formed within the wire lumen for directing the electrode wire or laser fiber outwardly away from the catheter body. To form ramp 300, the aperture 229 is first cut in the catheter body and silastic tubing 304 is then wrapped around the catheter body. A pre-curved mandrel 306 is then pushed through the silastic tubing and into wire lumen, and a straight mandrel 307 is inserted into the central lumen to maintain the configuration of the central lumen. Plastic filler 308 is then inserted into a distal end 310 of the wire lumen and heat is applied to the catheter to cause the plastic filler to form ramp 300 which is defined by one side 312 of the pre-curved mandrel. The mandrels and silastic tubing are then removed and the distal end of the catheter body is sealed. Alternatively, a spiral shaped conduit (not shown) is formed from the wire lumen through the catheter body.

Referring to FIGS. 36 and 37, a catheter 260 includes a catheter body 262 having a central lumen 264 and a wire lumen 266. Wire lumen 266 includes an opening 268 at a distal end of the catheter through which an electrode wire 270 can be extended. The electrode wire may be pre-curved such that when it is extended from the catheter body it conforms to a pre-curved shape 272. Again, the distal portion of the catheter body is constructed of sonolucent material and the extension of the wire is within a visualization range 274 of a transducer 276 disposed in the central lumen.

Once the wire is extended, RF energy may be applied to the wire and the wire (or the catheter) may be rotated (arrow 277) to provide a circular cut (not shown) or the catheter may be pushed or pulled to provide a linear cut. When the catheter is pushed or pulled, it may torque and cause a spiral rather than a linear cut. Alternatively, the catheter body includes a slot 278 along which the wire may be axially translated (arrow 280) while RF energy is applied to provide a straighter more controlled linear cut. The slot also allows the physician to precisely re-cut an incision.

The transducer is axially translatable (arrow 282) independent of the cutting wire and, prior to cutting, the transducer may be used to determine whether any crossing-vessels are present in the tissue surrounding the catheter. While cutting (circular or linear), the transducer may be translated relative to the cutting wire to keep the distal end of the cutting wire within the transducer's visualization range 274.

Alternatively, the electrode wire is replaced with a side fired laser fiber 284. once extended, the laser energy 286 emitted by the laser is used to cut the surrounding tissue. The laser fiber may be rotated (arrow 288) to provide a circular cut and may be axially translated (arrow 280) to provide a linear cut through slot 278. Again, the transducer is axially translatable independent of the laser fiber and may be used prior to cutting to determine if any crossing-vessels are present in the surrounding tissue. Similarly, while cutting, the transducer may be translated relative to the laser fiber to precisely position the laser fiber and to monitor the cut.

A full balloon (FIGS. 1 and 2) or a half-balloon (not shown) may be added to the above described catheters (FIGS. 28, 32, 36, and 38) to provide stabilization during the cutting procedure.

The transducers of the above described catheters may be simultaneously inserted within a patient with the catheter body or the catheter body may be inserted first and then the transducer may be inserted. Similarly, in the catheters of FIGS. 32, 36, and 38, the cutting elements, e.g., electrode wire or laser fiber, may be simultaneously inserted within a patient with the catheter body or the catheter body may be inserted first and then the cutting element may be inserted.

With reference to FIG. 39, there is shown another embodiment of a balloon catheter 400 in which balloon 402 is surrounded by a silicone sleeve 404. An electrosurgical electrode wire 406 extends through catheter shaft 408 and exits the catheter shaft through a wire port in the shaft at a location surrounded by silicone sleeve 404. Electrode wire 406 extends a short distance between balloon 402 and silicone sleeve 404, then exits through a wire port in silicone sleeve, and then re-enters through another wire port in silicone sleeve and extends a short distance further between balloon 402 and silicone sleeve 404 to a location near the distal tip of catheter shaft 408.

Silicone sleeve 404 insulates the bare, uninsulated electrode wire 406 except at locations along the length of balloon 402 where electrode wire 406 is exposed to tissue. In FIG. 39 balloon 402 is partially inflated, silicone sleeve 404 is partially expanded, liquid in vessel 416 is in the process of being displaced, and electrode wire 406 is almost in contact with the wall of vessel 416.

Consequently, electrode wire 406 is able to perform electrosurgical procedures in the internal wet vessels of the body such as the ureter. This is because current density of the circuit containing the electrode depends on the series impedance of the overall circuit as well as the material, design and type of tissue to be cut and the conditions of contact with the tissue. If a good conductor of electricity such as normal saline solution or urine is present, the saline solution or urine could cause a short circuit, thereby leaving little or no power to perform an electrosurgical cut. The embodiment of FIG. 39 basically preserves the current density of the circuit because the inflation of balloon 402 within the strictured ureter forces urine, saline and other forms of conductive liquids away from electrode wire 406 and the tissue to be cut, thereby averting a short circuit. Thus, a "dry zone" is created while the electrode wire is pressed against the wall of the vessel for full contact. Consequently, a lower, safer watt setting can be used to obtain an electrosurgical cut without loss of energy to liquid in the vicinity of the electrode wire.

If the embodiment of FIG. 39 is used in a ureter, balloon 402 is sized to be at least the same size as or larger in diameter than the ureter in order to assure full contact and complete evacuation of liquids. The balloon inflates, straightens, and dilates the ureter against the cutting wire to provide a straight aligned cut. Thus, the ureter takes the shape of the balloon.

In the event the stricture of the ureter is unable to be dilated by the balloon, the balloon will take the shape of the ureter, i.e., a waist shape, to displace the maximum amount of fluid. As the ureter stricture is cut, the pressure of the balloon will expand the ureter and the area of the cut will be kept "dry." Electrode wire 406 is positioned in the center of the dilatation length of balloon 402 in order to allow sealing to occur at the ends of the balloon in the event of balloon "waisting" or irregular shaping of the balloon.

One feature of the embodiment of FIG. 39 is that electrode wire 406 can be used to cut tissue at about 50 watts in a "dry zone," whereas in a "wet zone" about 150 watts would be required using the same electrode wire, which has a large surface area. This is an important safety feature because the electrode wire can be operated at low wattage and it will cut only in the "dry zone." Thus, accidental activation of electrical power, such as might occur by accidentally stepping onto the pedal of a power generator, will activate and short the electrode wire but will not cut the wall of the ureter when balloon 402 is not inflated or when catheter 400 is being delivered into the vessel, assuming electrode wire 406 is in a "wet zone" or "wet" area of contact.

With reference to FIG. 40, silicone sleeve 404 of the catheter of FIG. 39 has an inner diameter of about 0.066 inches, an outer diameter of about 0.086 inches, and a wall thickness of about 0.010 inches before it is inserted over the catheter shaft. Wire ports 412 and 414 may be integrally formed in silicone sleeve 404 or may be created by poking a sharp object through the silicone sleeve.

The silicone sleeve is immersed in freon at room temperature, which causes the silicone sleeve to swell and become slippery. The distal end of the catheter shaft is then inserted into the silicone sleeve and electrode wire is threaded through wire ports 412 and 414. The silicone sleeve will expand with the balloon and, in addition to acting as an electrical insulator, acts as a heat insulator under the exposed electrode wire to prevent rupture of the balloon. The silicone sleeve can collapse to a low profile having no wings.

The silicone sleeve together with the balloon can act as an acoustic coupling device for an ultrasound transducer when full contact is obtained between the balloon, the electrode wire and the ureter wall, which can be located within the catheter shaft as shown in the embodiments described above. The silicone sleeve thickness of 0.010 inches before expansion is sufficient to guarantee sonolucency through the silicone sleeve when it is expanded. The ultrasound transducer is used to view any underlying crossing vessels. If crossing vessels are present the electrode wire can be realigned. If no crossing vessel is present the electrode wire can be activated a longitudinal cut of about 2 centimeters achieved.

As an alternative to silicon, sleeve 404 could be manufactured from another elastic material such as rubber or latex.

With reference to FIG. 41, another embodiment of a balloon catheter 400 has an electrode wire 406 that is insulated everywhere except at its tip with standard wire insulation such as standard polyethylene or TEFLON. Electrode wire 406 might have a diameter of 0.018 inches without insulation and 0.030 inches with insulation. Only the tip 410 of electrode wire 406 is exposed, and the electrode wire is not attached to the distal end of the catheter. The electrode wire can be extended and contracted using a proximal handle (not shown). Balloon 402 is insulated with silicone sleeve 404, which covers both ends of the dilatation length of balloon 402. The distal point electrode wire 406 is activated when balloon 402 is inflated, thereby sandwiching electrode wire 406 between the tissue to be cut and silicone sleeve 404. The energized electrode wire is pulled in the proximal direction in the "dry zone," thereby cutting tissue. The contact surface area of the distal point of electrode wire 406 is small and thus current density at this point is great. Electrode wires of this type will short when conductors of electricity such as normal saline solution or urine are present, but will still have the power required to perform an electrosurgical cut. FIG. 41 shows balloon 402 partially inflated, silicone cover 404 partially expanded, liquids in the process of being displaced, and electrode wire 406 partially extended inside ureter 416.

FIG. 42 shows the silicone cover 402 of FIG. 41 prior to insertion of the catheter shaft of FIG. 41 into the silicone cover. Silicone cover 402 has a single wire port 412.

In an alternative embodiment electrode wire 406 of FIG. 41 could-be located completely externally of catheter 400, as a completely separate device positioned side by side with catheter 400 to achieve the same result as the embodiment of FIG. 41. Thus, electrode wire 406 does not have to be housed inside catheter shaft 408.

With reference to FIG. 43, in another embodiment catheter 400 includes an electrode wire 406 that is insulated up to its tip and includes a through lumen along its entire length. The electrode wire can be slid onto and along a wire guide 418 that is situated along the longitudinal dilatation length of balloon 402. Wire guide 418 (which is not used to deliver the catheter) may be a plastic wire having a diameter of, for example, 0.016 inches or an insulated metal wire. The through lumen of electrode wire 406 may have a diameter of 0.020 inches and the electrode wire (without insulation) may have an outer diameter of 0.026 inches. The insulated electrode wire may have an outer diameter of 0.028 inches if standard insulation is used or 0.027 inches if polyamide insulation is used. Once again, a silicone sleeve A04 is provided on balloon 402. Electrode wire 406 and wire guide 418 exit catheter shaft 408 and pass through a proximal portion of silicone sleeve 404, but electrode wire 406 and wire guide 418 could alternatively exit catheter shaft 408 at a location entirely proximal of silicone sleeve 404. This embodiment improves upon the embodiment of FIG. 41 in that the embodiment of FIG. 43 allows electrode wire 406 to be precisely controlled once catheter 400 is torqued.

RF current density is concentrated and directed to the distal tip of electrode wire 406. The electrode wire is pulled in the proximal direction along wire guide 418 to direct a cut into the ureter with balloon 402 providing support. The cut extends in a straight, guided path due to the presence of wire guide 418.

FIG. 44 shows the silicone sleeve 404 of the embodiment of FIG. 43.

FIG. 45 illustrates a top view of the distal tip 422 of the electrode wire 406 of the embodiment of FIG. 43. Stabilizer wings 420 are provided near distal tip 422 to ensure that the distal tip always faces away from the balloon. Stabilizer wings 420 slide along the surface of the silicone sleeve. Alternatively, if the stabilizer wings are used the silicone sleeve can be omitted because the distal tip will not face the balloon and therefore will not unduly heat and thereby rupture the balloon.

With reference to FIG. 46, there is shown an alternative to the embodiment of FIG. 43 in which electrode wire 406 engages wire guide 418 in a "monorail" fashion. Electrode wire 406 is insulated except at its tip and the electrode wire includes a short lumen 424 near its tip that engages wire guide 418. Electrode wire can be located external to catheter shaft 408 as shown or could alternatively be housed inside the length of the catheter shaft as shown in previously described embodiments. In the latter case stabilizer wings similar to those shown above in connection with FIG. 45 could be implemented at the distal tip of the electrode wire, with the possible elimination of silicone sleeve 404.

With reference to FIG. 47, there is shown yet another embodiment of a catheter 400 having an electrode wire 406 that is insulated in regions that would be exposed to liquid upon inflation of balloon 402 but that has a large non-insulated region where the inflated balloon would insulate electrode wire 406 from contact with electrically conductive liquid. In this embodiment a silicone cover 426 is attached to the catheter both proximal and distal of balloon 402 using a standard adhesive, the silicone cover 426 being positioned directly under electrode wire 406. Silicone cover 426 does not surround balloon 402 around its circumference however. This configuration provides a low-profile construction that is easy to manufacture.

With reference to FIG. 48, another embodiment of a catheter 400 includes a half balloon 402 and an electrode wire 406 that exits and re-enters catheter shaft 408 in a region corresponding to the inflated half balloon 402 but located on the side of catheter shaft 408 opposite to half balloon 402. No silicone sleeve or cover is required in this embodiment. Because electrode wire 406 rests on catheter shaft 408 there is no risk of heating and bursting balloon 402.

It is to be understood that all of the features described in detail with respect to the embodiment of FIG. 39 can be implemented in the embodiments of FIGS. 41, 43, and 46–48 where applicable.

There has been described a new and useful catheter for treatment of strictures (e.g., vessel). It will be appreciated by those skilled in the art that numerous departures from and modifications of the specific embodiments described herein may be made without departing from the spirit and scope of the claimed invention.

What is claimed is:

1. A catheter adapted to treat a vessel stricture, comprising:
   a catheter body of extended length constructed to be inserted within a body of a living being;
   an ultrasound imaging device disposed within a distal portion of said catheter body, said ultrasound imaging device being constructed to generate acoustic energy, to receive reflections of said acoustic energy, and to generate electrical signals in response thereto for use by an ultrasound imaging system constructed to display a real-time image, produced by said ultrasound imaging device, of tissue surrounding said distal portion of said catheter; and
   a cutting element comprising an electrode wire carried by said catheter body and being constructed to form a cut in said tissue,
   said ultrasound imaging device and said electrode wire adapted so that said real-time image includes said electrode wire in relation to said tissue.

2. The catheter of claim 1, further comprising a mechanism, connected to said catheter body and constructed to cause said cutting element to extend from said catheter body.

3. The catheter of claim 2, wherein said mechanism is a dilatation balloon.

4. The catheter of claim 3, wherein said mechanism further includes a syringe for inflating said dilatation balloon.

5. The catheter of claim 3, wherein said dilatation balloon is a mesh dilatation balloon.

6. The catheter of claim 5, wherein catheter body includes an inner catheter body and an outer catheter body and wherein said mechanism further includes a handle for moving said outer catheter body relative to said inner catheter body.

7. The catheter of claim 2, wherein said mechanism is constructed to advance said catheter body relative to a proximal portion of said cutting element and to cause a distal portion of said catheter body to bend.

8. The catheter of claim 2, wherein said mechanism is an axial translation device coupled to a proximal portion of said cutting element.

9. The catheter of claim 8, wherein said mechanism further includes:
   a hypo tube disposed in a lumen in said catheter body, wherein said hypo tube directs said cutting element outside said catheter body.

10. The catheter of claim 9, wherein said hypo tube further directs said cutting element outwardly away from said catheter body.

11. The catheter of claim 8, wherein said mechanism further includes:
    a ramp disposed in a lumen in said catheter body, wherein said ramp directs said cutting element outside said catheter body.

12. The catheter of claim 11, wherein said ramp further directs said cutting element outwardly away from said catheter body.

13. The catheter of claim 1, wherein said cutting element includes a distal portion and said distal portion of said cutting element is pre-curved.

14. The catheter of claim 1, wherein said cutting element includes a distal portion and said catheter body includes:
    a slot along which said distal portion of said cutting element is translated, wherein said cut is a linear cut.

15. The catheter of claim 1, wherein the catheter is adapted to remove a vessel stricture having a calcified region.

16. The catheter of claim 1, wherein said ultrasound imaging device is an ultrasound imaging transducer.

17. The catheter of claim 1, further comprising a motor coupler for coupling a drive shaft of said ultrasound imaging device to a motor, said motor being capable of rotating said drive shaft 360°, wherein rotation of said drive shaft rotates a transducer of said ultrasound imaging device such that said image is a 360° cross-section of a portion of said body of said living being surrounding said transducer.

18. The catheter of claim 1, wherein said cutting element includes a distal portion and said catheter body includes
    a stiff proximal portion having good torque transfer characteristics,
    a distal portion, and
    a sonolucent mid portion connected between said proximal portion and said distal portion and located adjacent to said distal portion of said cutting element.

19. The catheter of claim 18, wherein said stiff proximal portion includes a layer of braided polymer between two layers of polyethylene.

20. The catheter of claim 18, wherein said mid portion includes a layer of polyethylene.

21. The catheter of claim 1, wherein said catheter comprises a shaft having an axis and said cutting element is oriented longitudinal to the axis of the catheter shaft.

22. The catheter of claim 1, wherein said cutting element is adapted to provide a cut which is radially outward from said catheter body.

23. A catheter adapted to treat a vessel stricture, comprising:

a catheter body of extended length constructed to be inserted within a body of a living being;

an ultrasound imaging device disposed within a distal portion of said catheter body, said ultrasound imaging device being constructed to generate acoustic energy, to receive reflections of said acoustic energy, and to generate electrical signals in response thereto for use by an ultrasound imaging system constructed to display a real-time image, produced by said ultrasound imaging device, of tissue surrounding said distal portion of said catheter;

a cutting element comprising an electrode wire carried by said catheter body and being constructed to form a cut in said tissue;

a mechanism connected to said catheter body and constructed to cause said cutting element to extend outwardly away from said catheter body; and said ultrasound imaging device and said electrode wire adapted so that said real-time image includes said electrode wire in relation to said tissue.

24. The catheter of claim 23, wherein said electrode wire is constructed to generate electric current in tissue in proximity to said electrode wire, said electric current being sufficient to form said cut.

25. The catheter of claim 23, wherein said mechanism is a dilatation balloon.

26. The catheter of claim 25, wherein said mechanism further includes a syringe for inflating said dilatation balloon.

27. The catheter of claim 26, wherein said dilatation balloon is a mesh dilatation balloon.

28. The catheter of claim 27, wherein said catheter body includes an inner catheter body and an outer catheter body and wherein said mechanism further includes a handle for moving said, outer catheter body relative to said inner catheter body.

29. The catheter of claim 23, wherein said mechanism is constructed to advance said catheter body relative to a proximal portion of said cutting element and to cause a distal portion of said catheter body to bend.

30. The catheter of claim 23, wherein said mechanism is an axial translation device coupled to a proximal portion of said cutting element.

31. The catheter of claim 30, wherein said mechanism further includes:

a hypo tube disposed in a lumen in said catheter body, wherein said hypo tube directs said cutting element outside said catheter body.

32. The catheter of claim 30, wherein said mechanism further includes:

a ramp disposed in a lumen in said catheter body, wherein said ramp directs said cutting element outside said catheter body.

33. The catheter of claim 23, wherein said mechanism is adapted to allow a linear cut to be formed in the tissue with said cutting element.

34. The catheter of claim 23, wherein said mechanism is is adapted to allow a circular cut to be formed in the tissue with said cutting element.

35. The catheter of claim 23, wherein said mechanism is is adapted to allow a depth of a cut in the tissue to be increased with said cutting element.

36. A catheter adapted to treat a vessel stricture, comprising:

a catheter body of extended length constructed to be inserted within a body of a living being;

an ultrasound imaging device disposed within a distal portion of said catheter body, the distal portion including a sonolucent portion circumferentially surrounding the ultrasound imaging device, said ultrasound imaging device being constructed to generate acoustic energy for transfer through the sonolucent portion, to receive reflections of said acoustic energy through the sonolucent portion, and to generate electrical signals in response thereto for use by an ultrasound imaging system constructed to display a real-time image, produced by said ultrasound imaging device, of tissue surrounding said distal portion of said catheter;

a cutting element comprising an electrode wire carried by said catheter body and being constructed to form a cut in said tissue;

a mechanism connected to said catheter body and constructed to bring said cutting element into proximity with said tissue to form said cut in said tissue without adjustment of the position of said catheter body within said body of said living being or the position of said ultrasound imaging device within said catheter body; and said ultrasound imaging device and said electrode wire adapted so that said real-time image includes said electrode wire in relation to said tissue.

37. The catheter of claim 36, wherein said mechanism is a dilatation balloon.

38. The catheter of claim 37, wherein said mechanism further includes a syringe for inflating said dilatation balloon.

39. The catheter of claim 38, wherein said dilatation balloon is a mesh dilatation balloon.

40. The catheter of claim 39, wherein catheter body includes an inner catheter body and an outer catheter body and wherein said mechanism further includes a handle for moving said outer catheter body relative to said inner catheter body.

41. The catheter of claim 36, wherein said mechanism is constructed to advance said catheter body relative to a proximal portion of said cutting element and to cause a distal portion of said catheter body to bend.

42. The catheter of claim 36, wherein said mechanism is an axial translation device coupled to a proximal portion of said cutting element.

43. The catheter of claim 42, wherein said mechanism further includes:

a hypo tube disposed in a lumen in said catheter body, wherein said hypo tube directs said cutting element outside said catheter body.

44. The catheter of claim 42, wherein said mechanism further includes:

a ramp disposed in a lumen in said catheter body, wherein said ramp directs said cutting element outside said catheter body.

45. The catheter of claim 36, wherein said mechanism is is adapted to allow a linear cut to be formed in the tissue with said cutting element.

46. The catheter of claim 36, wherein said mechanism is is adapted to allow a circular cut to be formed in the tissue with said cutting element.

47. The catheter of claim 36, wherein said mechanism is adapted to allow a depth of a cut in the tissue to be increased with said cutting element.

48. A catheter adapted to treat a vessel stricture, comprising:

catheter body of extended length constructed to be inserted within a body of a living being, an ultrasound imaging device disposed within a distal portion of said catheter body, said ultrasound imaging device being constructed to generate acoustic energy, to receive reflections of said acoustic energy, and to generate electrical signals in response thereto for use by an ultrasound imaging system constructed to display a real-time image, produced by said ultrasound imaging device, of tissue surrounding said distal portion of said catheter, a cutting element carried by said catheter body and being constructed to form a cut in said tissue, and an axial translation device mechanically coupled with said ultrasound imaging device to permit longitudinal movement of said ultrasound imaging device with respect to said catheter body, and thereby to permit relative movement between said ultrasound imaging device and said distal portion of said cutting element so that said imaging device images said cutting element as well as said stricture.

49. The catheter of claim 48, wherein said cutting element is an electrode wire.

50. The catheter of claim 48, wherein said cutting element is a laser fiber.

51. The catheter of claim 48, further comprising a computer arranged to store images produced by said ultrasound imaging device as said ultrasound imaging device is moved along the length of the catheter body, said computer being capable of compiling the stored images into a three-dimensional image of said tissue surrounding the catheter body along the axial length of transducer travel.

52. The catheter of claim 48, further comprising a computer arranged to store images produced by said ultrasound imaging device as said ultrasound imaging device is moved along the length of the catheter body, said computer being capable of compiling the stored images into a series of two-dimensional images of said tissue surrounding the catheter body along the axial length of transducer travel.

53. The catheter of claim 48, wherein said image is a sonographic image.

54. The catheter of claim 48, wherein said image is a monographic image.

55. The catheter of claim 1, further including a dilatation balloon that is adapted to be expanded to cause vessel fluids in the area of the balloon to be displaced so as to create an essentially dry zone in the vessel, the electrode wire including an exposed conductive portion adapted to be located in the dry zone.

56. The catheter of claim 55, wherein the dilatation balloon includes a diameter sized to be at least as large as the diameter of the vessel when expanded.

57. The catheter of claim 55, wherein said electrode is adapted to cut tissue at a low power in the dry zone.

58. The catheter of claim 57, wherein said electrode is adapted to cut tissue in the dry zone at a power of about 50 watts.

59. The catheter of claim 55, wherein the electrode wire terminates in a distal tip including the exposed conductive portion.

60. The catheter of claim 59, wherein the catheter carries a guide wire, the electrode adapted to be carried by the guide wire.

61. The catheter of claim 59, wherein the electrode wire includes stabilizer wings near the distal tip.

62. The catheter of claim 55, wherein the balloon includes a sleeve made of a sonolucent insulative material that the electrode wire extends through.

63. The catheter of claim 62, wherein the sleeve is made of silicone.

64. The catheter of claim 1, further including a half balloon located on one side of the distal portion of the catheter body and the electrode wire located on an opposite side of the distal portion of the catheter body.

* * * * *